US008592662B2

(12) United States Patent
Todd, Jr. et al.

(10) Patent No.: US 8,592,662 B2
(45) Date of Patent: *Nov. 26, 2013

(54) CAPSICUM VARIETY EXHIBITING A HYPER-ACCUMULATION OF ZEAXANTHIN AND PRODUCTS DERIVED THEREFROM

(75) Inventors: Paul H. Todd, Jr., Kalamazoo, MI (US); James C. Melvin, legal representative, Kalamazoo, MI (US); Bradley E. Weller, legal representative, Kalamazoo, MI (US); Carrie Kay Young, Portage, MI (US); Anthony Vandenhombergh, Kalamazoo, MI (US); Donald Berdahl, Lawton, MI (US)

(73) Assignee: Kalamazoo Holdings, Inc., Kalamazoo, MI (US)

( * ) Notice: Subject to any disclaimer, the term of this patent is extended or adjusted under 35 U.S.C. 154(b) by 225 days.

This patent is subject to a terminal disclaimer.

(21) Appl. No.: 13/134,185

(22) Filed: Jun. 1, 2011

(65) Prior Publication Data

US 2011/0258744 A1    Oct. 20, 2011

Related U.S. Application Data

(63) Continuation-in-part of application No. 11/352,109, filed on Feb. 10, 2006, now abandoned.

(60) Provisional application No. 60/652,478, filed on Feb. 11, 2005.

(51) Int. Cl.
*A01H 5/00* (2006.01)
*A01H 1/00* (2006.01)
*C07H 21/04* (2006.01)
*C12N 15/00* (2006.01)

(52) U.S. Cl.
USPC ....... 800/317.1; 435/410; 530/370; 536/23.6; 800/260

(58) Field of Classification Search
USPC .......... 435/410; 530/370; 536/23.6; 800/260, 800/295, 317.1
See application file for complete search history.

(56) References Cited

U.S. PATENT DOCUMENTS

| | | |
|---|---|---|
| 3,539,686 A | 11/1970 | Rosenberg |
| 3,989,757 A | 11/1976 | Surmatis et al. |
| 3,998,753 A | 12/1976 | Antoshkiw et al. |
| 4,522,743 A | 6/1985 | Horn et al. |
| 4,952,716 A | 8/1990 | Lukac et al. |
| 5,107,065 A | 4/1992 | Shewmaker et al. |
| 5,180,747 A | 1/1993 | Matsuda et al. |
| 5,227,507 A | 7/1993 | Lukac et al. |
| 5,350,773 A | 9/1994 | Schweikert et al. |
| 5,356,636 A | 10/1994 | Schneider et al. |
| 5,506,353 A | 4/1996 | Subramaniam |
| 5,523,494 A | 6/1996 | Torres-Cardona et al. |
| 5,527,695 A | 6/1996 | Hodges et al. |
| 5,648,564 A | 7/1997 | Ausich et al. |
| 5,668,183 A | 9/1997 | Leuenberger |
| 5,773,075 A | 6/1998 | Todd |
| 5,786,017 A | 7/1998 | Blake et al. |
| 5,854,015 A | 12/1998 | Garnett et al. |
| 5,959,138 A | 9/1999 | Torres-Cardona et al. |
| 5,997,922 A | 12/1999 | Torres-Cardona et al. |
| 6,110,478 A | 8/2000 | Harang |
| 6,191,293 B1 | 2/2001 | Levy |
| 6,296,877 B1 | 10/2001 | Auweter et al. |
| 6,329,432 B2 | 12/2001 | Howard et al. |
| 6,329,557 B1 | 12/2001 | Rodriguez et al. |
| 6,376,722 B1 | 4/2002 | Sanz et al. |
| 6,504,067 B1 | 1/2003 | Montoya-Olvera et al. |
| 6,506,565 B1 | 1/2003 | Conner et al. |
| RE38,009 E | 2/2003 | Garnett et al. |
| 6,607,771 B2 | 8/2003 | Benczedi et al. |
| 6,635,293 B2 | 10/2003 | Fullmer et al. |
| 6,663,900 B2 | 12/2003 | DeFreitas et al. |
| 6,689,400 B2 | 2/2004 | Majeed |
| 6,784,351 B2 | 8/2004 | Hauptmann et al. |
| 2004/0010826 A1 | 1/2004 | Hauptmann et al. |

FOREIGN PATENT DOCUMENTS

| | | |
|---|---|---|
| WO | WO 9640092 | 12/1996 |
| WO | WO 9716175 | 5/1997 |
| WO | WO 02/060865 | 8/2002 |

OTHER PUBLICATIONS

Lai, et al., J. Sci. Food Agric 72:166-170, 1996.
Yokoi, Takiya Fragrance Journal, 20(5):36-42, 1992 (Abstract only).
Dictionary.com, accessed online 2010, Definition of Inbreeding, word origin 1835-45.
Webster's Third New International Dictionary, Definition of Inbreeding and Inbred, published 1963.
Brochure of the Aegean Agricultural Research Institute No. 1, three (3) pages; Aegean Agricultural Research Institute Pepper Database Accession, two (2) pages, 2000.
Wikipedia.org, accessed online 2010, "Classical Plant Breeding" description.
International Search Report, PCT/US2006/004880, Oct. 5, 2006.
Hanson, et al. Plant Genetics Resources (2004) 2:153-166.
Lee, et al. Scientia Horticulturae, (2005) 106:341-352.
Crosby, K. The Rewards of Breeding Vegetables That Are Fruits. Newsletter Vegetable and Fruit Improvement Center, (2002) vol. 6. No. 1.

(Continued)

*Primary Examiner* — Phuong Bui
(74) *Attorney, Agent, or Firm* — Hueschen and Sage

(57) ABSTRACT

The present invention is concerned with *Capsicum* plants producing greater than about 0.4% zeaxanthin, by weight in the dried, ripe fruit pod flesh, which plants have been developed from commercially grown *Capsicum* cultivars by plant breeding techniques. Zeaxanthin is the dominant carotenoid in the dried ripe fruit pod flesh, when measured in non-esterified forms. Alternatively, these plants may be characterized as exhibiting a high pigmentation measured as an ASTA value and further characterized by the predominant presence of zeaxanthin. The zeaxanthin derived from these *Capsicum* plants can be used in applications that include nutritional supplements, foods, functional foods, cosmetics, animal feeds, aquaculture feeds, and pharmaceuticals.

14 Claims, 3 Drawing Sheets

(56) References Cited

OTHER PUBLICATIONS

Vegetable and Fruit Improvement Center "The rewards of breeding vegetables that are fruits", vol. 6, No. 1, p. 1-4, 2002.

Hanson, et al., "Variation for antioxidant activity and antioxidants in a subset of AVRDC—the World Vegetable Center *Capsicum* core collection" Plant Genetic Resources Characterization and Utilization, vol. 2, No. 3, p. 153-166, Dec. 2004.

Howard, et al., "Changes in phytochemical and antioxidant activity of selected pepper cultivars (*Capsicum* Species) as influenced by maturity" Journal of Agricultural and Food Chemistry, vol. 48, No. 5, p. 1713-1720, May 2000.

Deli, et al., "Carotenoid composition in the fruits of *Capsicum annuum* Cv. Szentesi Kosszarvu during ripening" Journal of Agricultural and Food Chemistry, vol. 44, No. 3, p. 711-716, 1996.

Deli, et al., "Carotenoid composition in the fruits of red paprika(*Capsicum annuum* var. lycopersiciforme rubrum) during ripening; biosynthesis of carotenoids in red paprika" Journal of Agricultural and Food Chemistry, vol. 49, No. 3, p. 1517-1523, Mar. 2001.

Weller, et al., "Identification and quantification of zeaxanthin esters in plants using liquid chromatography-mass spectrometry" Journal of Agricultural and Food Chemistry, vol. 51, No. 24, p. 7044-7049, Nov. 19, 2003.

Lee, et al. "Impact of genetic and environmental variation on development of flavonoids and carotenoids in pepper(*Capsicum* supp.)" Scientia Gorticulturae, vol. 106, No. 3, p. 341-352, Oct. 3, 2005.

Collera-Zuniga, et al., "Comparative study of carotenoid composition in three Mexican varieties of *Capsicum annuum* L" Food Chemistry, vol. 90, No. 1-2, p. 109-114, Mar. 2005.

Kormos, et al. Acta Bot Acad Sci Hungaricae, 1960, vol. 6, No. 3/4, pp. 305-319, Abstract only.

Almela, Luis, et al.; J. Agric. Food Chem., vol. 44, No. 7, 1996, pp. 1705-1711.

Angelov, T.M. & Ribarowa, F.T.; Comptes rendus de l'Academie bulgare des Sciences, vol. 54, No. 5, 2001; pp. 69-72.

Balakrishnan, K.V., et al.; Acta Alimentaria, vol. 25(3), 1996; pp. 217-226.

Baranyai, M., et al.; Acta Alimentaria, vol. 11(3), 1982, pp. 309-323.

Biacs, Peter A., et al.; J. Agric. Food Chem. 1993, 41, pp. 1864-1867.

Biacs, Peter A. & Daood, Hussein G.; J. Plant Physiol., vol. 143, pp. 520-525 (1994).

Biacs, Peter A., et al.; J. Agric. Food Chem. 37, 1989, pp. 350-353.

Breithaupt, Dietmar Ernst & Schwack, Wolfgang; Eur Food Res Technol (2000), 211; pp. 52-55.

Breithaupt, Dietmar Ernst; Z. Naturforsch; 55c, (2000), pp. 971-975.

Burns, Jennifer, et al.; Phytochemistry, 62 (2003), pp. 939-947.

Camara, Bilal & Moneger, Rene; Phytochemistry, vol. 17, 1978, pp. 91-93.

Candela, M.E., et al.; Biologic Plantarium (Praha), 20(6), 1984, pp. 410-414.

Collera-Zuniga, Ofelia, et al.; Food Chemistry, 90 (2005), pp. 109-114.

White, James M.; Hori Science, 38(6), Oct. 2003.

Cserhati, Tibor, et al.; Journal of Chromatography A, 949 (2002) pp. 269-273.

Curl, Laurence A.; Agricultural and Food Chemistry, vol. 10, No. 6, Nov.-Dec. 1962, pp. 504-509.

Curl, Laurence A.; Journal of Agricultural and Food Chemistry, vol. 12, Nov.-Dec. 1964; The Carotenoids of Green Bell Peppers.

Cserhati, Tibor, et al.; Die Nahrung 39 (1995) 4, pp. 269-274.

Czinkotai, B., et al.; Chromatogram, Mar. 1989, pp. 4-5.

Czinkotai, B., et al.; Hournal of Liquid Chromatography, 12(14), pp. 2707-2717 (1989).

Davies, B.H., et al.; Phytochemistry, 1970, vol. 9, pp. 797-805.

Dela Mar, Rosalita R. & Francis, F.J.; Department of Food Science and Technology, University of Massachusetts, Amherst, Massachusetts,.1976, pp. 2-26; Carotenoid Degradation in Bleached Paprika.

Deli, Jozsef, et al.; J. Agric. Food Chem. 1996, 44, pp. 711-716.

Deli, Jozsef, et al.; J. Agric. Food Chem., 2001, 49, pp. 1517-1523.

Deli, J., et al.; Chromatographia Supplement vol. 56, 2002, pp. S-177-S-179.

Deli, J., et al.; Current Organic Chemistry, 6, (2002), pp. 1197-1219.

Deli, Jozsef, et al.; Eur Food Res Technol (2001), 213, pp. 301-305.

Deruere, Jean, et al.; The Plant Cell, vol. 6, pp. 119-133, Jan. 1994.

Fisher, Carolyn & Kocis, John A.; J. Agric. Food Chem. 1987, 35, pp. 55-57.

Hart, David J. & Scott, John; Food Chemistry, 54 (1995), pp. 101-111.

Holden, Joanne M., et al.; Journal of Food Composition and Analysis, 12, (1999), pp. 169-196.

Hornero-Mendez, Damaso, et al.; J. Agric. Food Chem. 2000, 48, pp. 3857-3864.

Marin, Alicia, et al.; J. Agric. Food Chem. 2004, 52, pp. 3861-3869.

Hornero-Mendez, D., et al.; "Color Modification During Paprika Processing" Amherst MA 1993; pp. 1-10.

Hornero-Mendez, Damaso & Minguez-Mosquera, Isabel; J. Agric. Food Chem. 2000, 48, pp. 1617-1622.

Howard, L.R., et al.; J. Agric. Food Chem, 2000, 48, pp. 1713-1720.

Huh, J.H., et al.; Theor Appl Genet (2001), 102, pp. 524-530.

Jaren-Galan, Manuel, et al.; J. Agric. Food Chem. 1999, 47, pp. 3558-3564.

Jaren-Galan, Manuel & Minguez-Mosquera, Isabel; J. Agric. Food Chem., 1999, 47, pp. 4379-4383.

Levy, Arieh, et al.; J. Agric. Food Chem., 1995, 43, pp. 362-366.

Kim, S., et al.; Journal of Food Science, vol. 69, No. 1, 2004, pp. C39-C44.

Klaui, H & Bauernfield, J.C.; Carotenoids as Colorants and Vitamin A Precursors:Technological and Nutritional Applications, 1981, pp. 66-103.

Krishnamurthy, M.N. & Natarajan, C.P.; Indian Food Packer, Jan.-Feb. 1973, pp. 39-44; "Colour and Its Changes in Chillies".

Lee, Jinsuk J., et al.; Scientia Horticulturae, 106 (2005), pp. 341-352.

Lord, C.E.C. & Tirimanna, A.S.L.; Mikrochimica Acta [Wien], 1976, vol. 1, No. 4-5, pp. 469-476.

Mangels, Ann Reed, et al.; Journal of the American Dietetic Association, vol. 93, No. 3, Mar. 1993, pp. 284-296.

Markus, F., et al.; J. Agric. Food Chem, 1999, vol. 47, No. 1, pp. 100-107.

Matus, Zoltan, et al.; J. Agric. Food Chem, 1991, vol. 39, No. 11, pp. 1907-1914.

Minguez-Mosquera, M. Isabel & Hornero-Mendez, Damaso; J. Agric. Food Chem., 1994, vol. 42, No. 3, pp. 640-644.

Minguez-Mosquera, M. Isabel & Hornero-Mendez, Damaso; J. Agric. Food Chem., 1994, vol. 42, No. 1, pp. 38-44.

Minguez-Mosquera, M.I., et al.; J. Agric. Food Chem., 1994, vol. 42, No. 5, pp. 1190-1193.

Minguez-Mosquera, M. Isabel & Hornero-Mendez, Damaso; J. Agric. Food Chem., 1993, Vo. 41, No. 10, pp. 1616-1620.

Muller, Harald; Z Lebnsm Unters Forsch A (1997), 204, pp. 88-94.

Murkovic, M., et al.; Journal of Food Composition and Analysis (2000), 13, pp. 435-440.

Perez-Galvez, Antonio, et al.; J. Agric. Food Chem., 2004, vol. 52, No. 3, pp. 518-522.

Perez-Galvez, Antonio, et al.; J. Agric. Food Chem., 2004, vol. 52, No. 3, pp. 632-637.

Perez-Galvez, Antonio, et al.; British Journal of Nutrition, (2003), 89, 787-793.

Almela, Luis, et al.; J. Agric. Food Chem., 1991, vol. 39, No. 9, pp. 1606-1609.

Perucka, Irena; Pol. J. Food Nutr. Sci., 1996, vol. 5/46, No. 4, pp. 61-68.

Pfander, H, et al.; Studia Univ. Babes-Bolyai, Chemia, XXXIX, 1-2, 1994, pp. 70-77.

J.W. Pursegloves, 1981, Spices, vol. 1, Longman: New York, pp. 372-389.

Rahman, F.M.M. & Buckle, K.A.; J. Fd. Technol. (1980), 15, pp. 241-249.

D. Couillaud,et al., 1998, Determination of Caratenoids in Paprika, Journal: Rivista Italiana EPPOS, pp. 531-537.

Romer, S., et al.; Metabolic Engineering, (2002), 4, pp. 263-272.

Scalia, S. & Francis, G.W.; Chromatographia, vol. 28, No. 3, Aug. 1989, pp. 129-132.

Schweiggert, Ute, et al.; Rapid Commun. Mass Spectrom., 2005, 19, pp. 2617-2628.

(56) References Cited

OTHER PUBLICATIONS

Varga, L., et al.; Acta Alimentaria, (1984), vol. 13 (4), pp. 295-302.
Vesper, Hubert & Nitz, Siegfried; Adv Food Sci (CMTL), (1997), vol. 19, No. 5/6, pp. 178-183.
Vesper, Hubert & Nitz, Siegfried; Adv Food Sci (CMTL), (1997), vol. 19, No. 3/4, pp. 124-130.
Vinkler, M. & Kiszfl-Richter, M; Acta Alimentaria Academia, vol. 1, Issue 1, (1972), pp. 41-51.
Weissenberg, M., et al.; Journal of Chromatography A, 757 (1997), pp. 89-95.
Zorn, Holger, et al.; Enzyme and Microbial Technology, 32 (2003), pp. 623-628.
Zachariv, Gy., et al.; Acta Alimentaria, vol. 20, (2), (1991), pp. 115-122.
Abel, R.Jr.,2004, The Eye Care Revolution: Prevent and Reverse Common Vision Problems, Kensington Publishing Corp., NY, NY ISBN 0-7582-0622-4, p. 159.
Abellan-Palazon, M., 2001, Effect of Titanium Ascorbate Treatment on Red and Yellow Pigment Composition of Paprika Cultivars, Acta Alimentaria, vol. 30 (2), pp. 159-171.
Ahmed S. et al., 2005, The Macular Xanthophylls. Surv Ophthalmol., 50(2), pp. 183-193.
Almela, L. et al., 1991, Carotenoid Composition of New Cultivar of Red Pepper for Paprika, J. Agric. Food Chem., 39, pp. 1606-1609.
Almela, L. et al., 1996, Changes in Pigments, Chlorophyllase Activity and Chloroplast Ultrastructure in Ripening Pepper for Paprika, J. Agric. Food Chem. 44, pp. 1704-1711.
Alves-Rodrigues A, and Shao A., 2004, The Science Behind Lutein. Toxicol Lett. Apr. 15, 150(1), pp. 57-83.
Antony, J. I. X and Shankaranarayana, M.L., 2001, Lutein—A Natural Colorant and a Phytonutrient for Eye Health Protection, The World of Food Ingredients, Apr./May, pp. 64-67.
Aranson, J. T. et al., 1995, Fate of Phototoxic Terthiophene Insecticides in Organisms and the Environment in Light-Activated Pest Control, ACS Symposium Series 616, J.R. Heitz and K.R. Downum, eds., American Chemical Society, Washington DC, pp. 143-151.
Banaras, M. et al., 1994, Relationship of Physical Properties to Postharvest Water Loss on Pepper Fruits (*Capsicum annuum* L.), Pak. J. Bot., 26(2), pp. 321-326.
Beatty S. et al., 2004, Macular Pigment Optical Density and Its Relationship With Serum and Dietary Levels of Lutein and Zeaxanthin. Arch Biochem Biophys., 430(1), pp. 70-76.
Biacs, P. et al., 1993, Carotenoids and Carotenoid Esters from New Cross-Cultivars of Paprika, J. Agric. Food Chem., 41, pp. 1864-1867.
Biacs, P. and Daood, H., 1994, High Performance Liquid Chromatography with Photodiode-array Detection of Carotenoids and Carotenoid Esters in Fruits and Vegetables, J. Plant Physiol. vol. 143, pp. 520-525.
Brown L. et al., 1999, A Prospective Study of Carotenoid Intake and Risk of Cataract Extraction in US Men. Am J Clin Nutr., 70(4), pp. 517-524.
Bouvier F, et al., 1994, "Xanthophyll Biosynthesis in Chromoplasts: Isolation and Molecular Cloning of an Enzyme Catalyzing the Conversion of 5,6-Epoxycarotenoid Into Ketocarotenoid," Plant Journal 6, pp. 45-54.
Bowen, P. E., et al., 2002, Esterification Does Not Impair Lutein Bioavailability in Humans, J. Nutr. 132, pp. 3668-3673.
Breithaupt, D. E., and Bamedi, A., 2001, Carotenoid Esters in Vegetables and Fruits: A Screening with Emphasis on β-Cryptoxanthin Esters, J. Agric. Food Chem., 49, pp. 2064-2070.
Connor S. et al., 2004, Diets Lower in Folic Acid and Carotenoids Are Associated with the Coronary Disease Epidemic in Central and Eastern Europe. J Am Diet Assoc. 104(12): pp. 1793-1799.
Davies, N. P. et al., 2004, Macular Pigments: Their Characterization and Putative Role, Prog. Ret. Eye Res. 23, pp. 533-559.
Deli, J. et al., 1992, Carotenoid Composition in the Fruits of Black Paprika (*Capsicum annuum* Variety *longum nigrum*) during Ripening, J. Agric. Food Chem., 40, pp. 2076.
Deli, J. et al., 1996, Carotenoid Composition in the Fruits of *Capsicum annuum* Cv. Szentesi Kosszarvu during Ripening, J. Agric. Food Chem., 44, pp. 711-716.
Deli, J., and G. Toth, 1997, Carotenoid Composition of the Fruits of *Capsicum annuum* Cv. Bovet 4 During Ripening, Z Lebensm Unters Forsch A, 205, pp. 388-391.
Deli, J. et al., 2001, Carotenoid Composition in the Fruits of Red Paprika (*Capsicum annuum* var. *lycospersiciforme rubrum*) During Ripening: Biosynthesis of Carotenoids in Red Paprika, J. Agric. Food Chem., 49, pp. 1517-1523.
Downum, K.R. and J. Wen, "The Occurrence of Photosensitizers Among Higher Plants", in *Light-Actived Pest Control*, ACS Symposium Series 616, J.R. Heitz and K.R. Downum, eds., American Chemical Society, Washington DC, pp. 135-143.
Deruere, J., et al., 1994, The Plant Cell, vol. 6, pp. 119-113.
Englert, G. et al, 1991, Helv. Chim. Acta., 74, pp. 969-982.
Evans et al., 1993, Handbook of Plant Cell Culture, MacMillian Publishing Co., NY.
Fisher, C. and Kocis, J.A., 1987, *J. Agric. Food Chem.* 35, pp. 55-57.
Gelvin et al., 1990, Plant Molecular Biology Manual, Kluwer Academic Publishers.
Green et al., 1987. Plant Tissue & Cell Culture, Academic Press, NY.
Hausen, B. M., and B. Helmke, 1995, "Butenylbithiophene, α-terthienyl and Hydroxytremetone As Contact Allergens in Cultivars of Marigold (*Tagetes* sp.)," Cont. Derm. 33, pp. 33-37.
Hirschberg, J., 2001, "Carotenoid Biosynthesis in Flowering Plants," Current Opinions in Plant Biology 4(3), pp. 210-218.
Hornero-Mendez, D. et al., 2002, "Characterization of Carotenoid High-Producing *Capsicum annuum* Cultivars Selected for Paprika Production," J. Agric. Food Chem., 50, pp. 5711-5716.
Ishida, B. K., et al, 2005, Assessing Bioavailability of cis- vs trans-lycopene isomers in Tangerine and Red Tomatoes, Carotenoid Science, vol. 9, pp. 92.
Isler, O. et al, 1956, Helv. Cim. Acta., 39, p. 249.
Ito Y, et al, 2005, JACC Study Group. Lung Cancer Mortality and Serum Levels of Carotenoids, Retinol, Tocopherols, and Folic Acid in Men and Women: A Case-Control Study Nested in The JACC Study. J Epidemiol. Suppl 2:S140-9. PMID: 16127226.
Kahl et al., (1995) World Journal of Microbiology and Biotechnology 11, pp. 449-460.
Karrer, P. and Jucker, E., 1950, *Carotenoids*, Elsevier Publ. Co., Inc., Amsterdam, pp. 38-42, 180 ff.
Khachik, F. et al., 1992, Isolation and Structural Elucidation of the Geometrical Isomers of Lutein and Zeaxanthin in Extract from Human Plasma, J. Chromatogr. Biomed. Appl. 582, pp. 153-166.
Khachik, F., et al., 1995, Lutein, Lycopene, and Their Oxidative Metabolites in Chemo-prevention of Cancer, J. Cell. Biochem., Suppl. 22, pp. 236-246.
Khachik F, et al., 1997, Identification of Lutein and Zeaxanthin Oxidation Products in Human and Monkey Retinas. Invest Ophthalmol Vis Sci., pp. 1802-1811.
Khachik, F. et al., 1999, Dietary Carotenoids and their Metabolites as Potentially Useful Chemoprotective Agents against Cancer, in Antioxidant Food Supplements in Human Health, L. Packer, M. Hiramatsu and T. Yoshikawa, eds., Academic Press, NY, pp. 203-229.
Klee et al., 1987, Ann. Rev. of Plant Phys. 38, pp. 467-486.
Kohlmeier, L. et al., 1995, Am. J. Clin. Nutr.62, pp. 137-146.
Levy, Joseph, et al., 1995, Lycopene Is a More Potent Inhibitor of Human Cancer Cell Proliferation Than Either α-Carotene or β-Carotene, Nutrition & Cancer, pp. 257-266.
Lutein and Zeaxanthin Scientific Review, Roche Vitamins Technical Publication HHN-1382/0800 (2000).
Lyle BJ, et al., 1999, Antioxidant Intake and Risk of Incident Age-Related Nuclear Cataracts in The Beaver Dam Eye Study., Am J Epidemiol., pp. 801-809.
Matus et al., 1991, Carotenoid Composition of Yellow Pepper during Ripening: Isolation of β-Cryptoxanthin 5,6-Epoxide, J. Agric. Food Chem., 39, pp. 1907-1914.
Minguez-Mosquera, M. I. et al., 1993, Effect of Processing of Paprika on the Main Carotenes and Esterified Xanthophylls Present in the Fresh Fruit, J. Agric. Food Chem., 41, pp. 2120-2124.

(56) References Cited

OTHER PUBLICATIONS

Minguez-Mosquera, M. I. et al., 1994, Comparative Study of the Effect of Paprika Processing on the Carotenoids in Peppers (*Capsicum annuum*) of the *Bola* and *Agridulce* Varieties, J. Agric. Food Chem., 42, 1555-1560.
Minguez-Mosquera, M. and•Hornero-Mendez, D., 1994, Changes in Carotenoid Esterification during the Fruit Ripening of *Capsicum annuum* Cv. *Bola*, J. Agric. Food Chem., 42, pp. 640-644.
Minguez-Mosquera, M. and Hornero-Mendez, D., 1993 Separation and Quantification of the Carotenoid Pigments in Red Peppers (*Capsicum annuum* L.), Paprika, and Oleoresin by Reversed-Phase HPLC, J. Agric. Food Chem., 41, pp. 1616-1620.
Muller, H., 1997, Determination of the carotenoid content in selected vegetables and fruit by HPLC and Photodiode array detection, Z. Lebensm Unters Forsch A., 204, pp. 88-94.
Murakoshi et al., 1992, Cancer Res., 52, pp. 6583-6587.
Nys, Y. Arch. Geflugelk, 2000, 64 (2), pp. 45-54.
Osganina S., et al., 2003, Dietary Carotenoids and Risk of Coronary Artery Disease in Women, Am. J. Clin. Nutr. Jun. 2003;77(6), pp. 1390-1393.
Packer. L. et al., (Editors), 1999, Antioxident Food Supplements in Human Health, Academic Press, NY, pp. 223-226.
Pattison, D., 2005, American Journal of Clinical Nutrition, Pub. by American Society for Clinical Nutrition, vol. 82, No. 2, pp. 451-455.
Rahman, R. M. M., and K. A. Buckle, 1980, "Pigment Changes in *Capsicum* Cultivars During Maturation and Ripening", J. Fd. Technol., 15, pp. 241-249.
Ribaya-Mercado J. et al., 2004, Lutein and Zeaxanthin and Their Potential Roles in Disease Prevention. J. Am. Coll. Nutr., 23(6 Suppl), pp. 567S-587S.
Rock C. et al., 2005, Plasma Carotenoids and Recurrence-free Survival in Women with a History of Breast Cancer. J. Clin. Oncol., pp. 6631-6638.
Russo, V.M. and Howard, L.R. (2002) *J. Sci. Food Agric.* 82: 615-624.
Seddon, J.M. et al., 1994, Dietary Carotenoids, Vitamins A, C, and E, and Advanced Age-Related Macular Degeneration, J. Am. Med. Assoc. 272(9), pp. 1413-1420.
Stahl W., 2005, Macular Carotenoids: Lutein and Zeaxanthin. Dev Ophthalmol. 38, pp. 70-88.
Stahl W. and Sies H., 2005, Bioactivity and Protective effects of Natural Carotenoids. Biochim Biophys Acta., 1740(2), pp. 101-107. Epub Dec. 28, 2004.
Stringham J. and Hammond B. Jr., 2005, Dietary Lutein and Zeaxanthin: Possible Effects on Visual Function, Nutr. Rev. 63(2), pp. 59-64.
Tanaka et al., 1994, Carcinogenesis 15, pp. 15-19.
Topuz, A. and Ozdemir, F., 2003, Influences of γ-Irradiation and Storage on the Carotenoids of Sun-Dried and Dehydrated Paprika, J. Agric. Food Chem., 51, pp. 4972-4977.
Updike, A. A., and Schwartz, S. J., 2003, Thermal Processing of Vegetables Increases the Cis Isomers of Lutein and Zeaxanthin, J. Agric. Food Chem. 51, pp. 6184-6190.
Vasil., 1984, Cell Culture and Somatic Cell Genetics of Plants, vol. I, II, III, Laboratory Procedures and Their Applications, Academic Press, NY.
Weissbach and Weissbach, 1989, Methods for Plant Molecular Biology, Academic Press.
Weller, P. and Breithaupt, D., 2003, Identification and Quantification of Zeaxanthin Esters in Plants Using Liquid Chromatography—Mass Spectrometry, J. Agric. Food Chem., 51, pp. 7044-7049.
Yin et al., 2004, Transgene Inheritance in Plants. J. Appl. Genet. 45(2), pp. 127-144 and references therein.
Zechmeister, L., 1962, *Cis-Trans Isomeric Carotenoids Vitamins A and Arylpolyenes*, Academic Press, pp. 46-57.
Zhou, L. et al., 1999, The Identification of Dipalmityl Zeaxanthin as the Major Carotenoid in Gou Qi Zi by High Pressure Liquid Chromatography and Mass Spectrometry, J. Ocular Pharm. and Therap., 15(6), pp. 557-565.
Sommerburg, Olaf, et al.; Br F Ophthamol, 1999, 82, pp. 907-910.
Camara, Bilal & Moneger, Rene; Phytochemistry, 1978, vol. 17, pp. 91-93.
Breithaupt, Dietmar E., et al.; British Journal of Nutrition, (2004), 91, pp. 707-713.
Breithaupt, Dietmar E. & Schlatterer, Jorg; Eur Food Res Technol, (2005) 220, pp. 648-652.
Anthony, J.I.X., Dr. & Shankaranarayana, M.L., Dr.; The World of Food Ingredients; Apr./May 2001, pp. 64-67; "Lutein, A natural colourant and a phytonutrient for eye health protection".
Arnason, J.T., et al.; American Chemical Society, 1989; Chapter 12, pp. 164-172; "Naturally Occurring and Synthetic Thiophenes as Photoactivated Insecticides".
Arroo, R.R.J., et al.; Plant Cell Report; 1995, vol. 15, pp. 133-137.
Boch, R., et al.; Journal of Photochemistry and Photobiology A: Chemistry 93 (1996) pp. 39-47.
Downum, Kelsey R. and Wen, Jinghai; American Chemical Society, 1995; ACS Symposium Series 616; "Light-Activated Pest Control"; Chapter 11, pp. Cover, 134-143.
Hausen, Bjorn M. & Helmke, Burkhard; Contact Dermatits, 1995, 33, pp. 33-37.
Khachik, Frederick, Ph.D., et al.; Journal of Cellular Biochemistry, Supplement 22, (1995), pp. 236-246.
Marles, R., et al.; Pharmacology & Toxicology, 1995, 77, pp. 164-168.
Mordi, Raphael C.; Chemistry & Industry, Feb. 1, 1993, pp. 79-83; "Carotenoids: Functions and Degradation".
Nivsarkar, Manish; Current Science, vol. 76, No. 10, May 25, 1999; pp. 1391-1393.
Paulsen, Evy; Contact Dermatitis, 2002, 47, pp. 189-198.
Rampone, William M., et al.; The Society for Investigative Dermatology, Inc., vol. 87, No. 3, Sep. 1986, pp. 354-357.
Guzman, et al., Plant Science 179 (2010) 49-59.

Representative HPLC chromatogram of saponified ground *Capsicum* from Example 8.

Representative HPLC chromatogram of saponified *Capsicum* oleoresin from Example 8.

CAPSICUM VARIETY EXHIBITING A HYPER-ACCUMULATION OF ZEAXANTHIN AND PRODUCTS DERIVED THEREFROM

FIELD OF THE INVENTION

The present invention is concerned with *Capsicum* plants producing greater than about 0.4% zeaxanthin, by weight in dried, ripe fruit pod flesh, which plants have been developed from commercially grown *Capsicum* cultivars by plant breeding techniques. Zeaxanthin is the dominant carotenoid found in the dried ripe fruit pod flesh, when measured in non-esterified forms. Alternatively, these plants may be characterized as exhibiting a high pigmentation measured as an ASTA value and further characterized by the predominant presence of zeaxanthin. The zeaxanthin derived from these *Capsicum* plants can be used in applications that include nutritional supplements, foods, functional foods, cosmetics, animal feeds, aquaculture feeds, and pharmaceuticals.

BACKGROUND OF THE INVENTION

The ripe fruit of *Capsicum* species are a well-known, important source of a variety of carotenoids, including oxygenated carotene derivatives, commonly referred to as xanthophylls. *Capsicum* species contain capsanthin, capsorubin, cryptocapsin, zeaxanthin, lutein, and other carotenoids that have substantial nutritional and medical value. Epidemiological studies have shown that frequent and regular consumption of carotenoids reduces risks of chronic disorders, such as cardiovascular diseases [Kohlmeier et al. (1995)] or cancer [Murakoshi et al., (1992); Levy et al. (1995); Tanaka et al., 1994) Ito et al. (2005), Connor et al. (2004), and Rock et al. (2005)]. Carotenoids may also function as antioxidants in disease prevention. Both zeaxanthin and lutein are reported to possess strong anti-tumor properties [Packer et al. (1999)]. Epidemiologic studies suggest that the antioxidant potential of dietary carotenoids may protect against the oxidative damage that can result in inflammation. A modest increase in dietary carotenoid intake is associated with a reduced risk of developing inflammatory disorders such as rheumatoid arthritis [Pattison, et al. (2005)].

A higher dietary intake of carotenoids is also associated with a lower risk for AMD (Age-related Macular Degeneration) occurring in older adults. Hereditary forms with an early onset include Stargardts, Best's Disease and progressive Cone Dystrophy. Hereditary retinal degenerations that attack the whole of the retina tend to be more severe. The most common types of these diseases are Retinitis Pigmentosa, Choroideremia, Ushers Syndrome and diabetic retinopathy. Individuals consuming the highest levels of carotenoids exhibit a 43% (statistically significant) lower risk for AMD [Seddon et al., (1994). The specific carotenoids, zeaxanthin and lutein, are most strongly associated with a reduced risk for AMD. Zeaxanthin and lutein are the sole xanthophyll pigments found in the retina and concentrated in the macula. Excellent reviews of the role of carotenoids in the macula are found in Davies, et al., 2004, Stahl et al. (2005), Stringham et al. (2005), Ahmed et al. (2005), Stahl (2005), Beatty et al. (2004), Davies (2004), and Alves-Rodrigues (2004).

There is a strong association between higher consumption of dark green vegetables, which contain xanthophylls, including zeaxanthin and lutein, and a decreased risk for light-induced oxidative eye damage, such as cataract formation, see Brown et al. (1999) and Ribaya-Mercado (2004). Although dark green vegetables are an excellent dietary source of zeaxanthin and lutein, the isolation and purification of these compounds in large quantities from green vegetables is time-consuming and costly. Twenty-five grams of a fresh, dark green vegetable such as kale theoretically provide 10 mg of lutein. (Khachik et al. 1995). Corn, one of the highest plant sources of zeaxanthin, contains 0.528 mg of zeaxanthin per 100 grams of corn (Lutein and Zeaxanthin Scientific Review, Roche Vitamins Technical Publication HHN-1382/0800). It would require 1.9 kg of corn or 0.623 kg of peppers to provide 10 mg of zeaxanthin from these sources.

Therefore, a highly concentrated source of natural zeaxanthin is needed for the manufacture of dietary supplements and functional foods. Moreover, zeaxanthin is an important ingredient to add color to foods and as an additive in animal feeds to color poultry skin, egg yolks, fish flesh and the like. A natural source of zeaxanthin that can be used in foods is preferred and/or regulated over a synthetic product in these applications.

"GRAS" is an acronym for the phrase Generally Recognized As Safe. Under sections 201(s) and 409 of the Federal Food, Drug, and Cosmetic Act (the Act), any substance that is intentionally added to food is a food additive, that is subject to premarket review and approval by FDA, unless the substance is generally recognized, among qualified experts, as having been adequately shown to be safe under the conditions of its intended use, or unless the use of the substance is otherwise excluded from the definition of a food additive. Regardless of whether the use of a substance is a food additive use or is GRAS, there must be evidence that the substance is safe under the conditions of its intended use. FDA has defined "safe" (21 CFR 170.3(i)) as a reasonable certainty in the minds of competent scientists that the substance is not harmful under its intended conditions of use. The specific data and information that demonstrate safety depend on the characteristics of the substance, the estimated dietary intake, and the population that will consume the substance.

Zeaxanthin derived from natural sources is usually obtained as a mixture of free xanthophyll compounds together with the pigment in the form of mixtures of mono and diesters of fatty acids. The fatty acids generally contain from eight to twenty carbon atoms. Methods for converting these esterified forms of zeaxanthin to a free alcohol form are well known and documented. Methods for preparing esters from the non-esterified form are also known and documented.

Zeaxanthin from natural sources is generally obtained in the form of an all-trans isomer. It is well known that the trans isomer can be converted to cis forms by the application of heat and/or light or by the addition of a catalytic amount of iodine (Zechmeister, 1962; Khachik, et al. 1992; Updike et al., 2003; Englert, et al. 1991 and references therein; Karrer and Jucker, 1950. Zechmeister also discusses isomerization by acid catalysts, contact with active surfaces, via boron trifluoride complexes and bio-stereoisomerization. Given the number of double bonds in the structure, a large number of different cis isomers are possible. Both cis and trans isomers have been detected in the retina.

Zeaxanthin also exists in two enantiomeric and one meso form, namely 3R,3'R; 3S,3'S and 3R,3'S (note 3S,3'R is identical to 3R,3'S). All three stereoisomers have been found in the human retina (U.S. Pat. No. 6,329,432), but the 3R,3'R isomer is dominant. It is difficult to separate these three isomers of zeaxanthin from each other in commercial quantities for human consumption. Therefore, for synthetic production of zeaxanthin, either a chiral process or a chiral separation process is needed in order to purify and produce the 3R,3'R stereoisomer.

Age-related Macular Degeneration (AMD) is the leading cause of blindness for people older than 65 in the United States, and is expected to affect 40 million U.S. residents by the year 2030 [Abel, (2004). Treatments to ameliorate the effects of the disease and methods for preventing the onset of the disease are desperately needed. Since lutein and zeaxanthin play a critical role in the protection of the macula, it is important that people have access to these compounds, either through dietary sources, through supplements, or through so-called functional foods, which foods contain enhanced levels of these nutrients. Numerous epidemiological studies suggest that the typical intake of lutein and zeaxanthin is only in the 1-3 mg/day range, see Brown et al. (1999) and Lyle et al. (1999). Seddon et al. (1994) reported a relationship between the intake of lutein and zeaxanthin at 6 mg per day and a decreased risk of AMD and cataracts. This dietary gap of 3-5 mg per day can be eliminated with the use of supplements.

There is a perceived need in the marketplace for naturally derived zeaxanthin, as opposed to synthetic zeaxanthin, that can serve as a dietary source in the form of a dietary supplement, a food or beverage additive, or a food or beverage colorant. Furthermore, there is a need for zeaxanthin for dietary supplements, food or beverage additives, and food or beverage colorants in biologically available forms.

There is also a need for naturally derived zeaxanthin, as opposed to synthetic zeaxanthin, that can serve as an additive in animal feeds, such as poultry feed, to color flesh and skin, egg yolks and fish flesh. Certain types of poultry feed additives prepared from corn gluten contain a relatively high percentage of zeaxanthin (about 15-30%), when measured as a percentage of total carotenoids. However, the total carotenoid content of these feed additives is very low (only about 100 milligrams of total carotenoids per pound of poultry feed). Another type of poultry feed additive is prepared from marigold extracts. This additive contains roughly 100-200 times as much yellow pigment per pound of additive (i.e., about 10 to 20 grams of lutein and zeaxanthin per pound); however, more than 95% of the yellow pigment in this marigold preparation is lutein, not zeaxanthin. Zeaxanthin comprises only about 2 to 5% of the yellow pigment in this poultry feed additive (U.S. Pat. No. RE 38,009).

Genetics

The accumulation of carotenoids in *Capsicum* fleshy fruit is well studied, with many known biosynthetic genes cloned, sequenced and functionally characterized on some level. Although the majority of investigations into carotenoid biosynthesis has been carried out in the model system *Solanum lycopersicon* (tomato), additional work has shown a high level of conservation of these genes among all plant species accumulating carotenoids [Hirschberg (2001)]. Also, certain carotenoids show taxonomic specificity. For example, capsanthin and capsorubin are responsible for the red color seen in ripe pods of *Capsicum*, and are not seen in any other genus. These two carotenoids are synthesized via the action of capsanthin-capsorubin synthase (Ccs) from antheraxanthin and violaxanthin respectively. In the absence of Ccs, peppers do not accumulate significant amounts of capsanthin or capsorubin and the resulting ripe fruit are orange in color [Bouvier, et al., (1994)].

The dietary supplement marketplace in both the US and in Europe does not accept nutrients that are derived from genetically modified organisms. Therefore, there is a need for a naturally derived zeaxanthin product that is not derived from a genetically modified plant.

Currently, zeaxanthin is available from a number of sources. It is produced synthetically, extracted from plant matter and extracted from bacteria.

Synthetic Zeaxanthin

The all-trans 3R,3R' zeaxanthin isomer is produced synthetically, and a process for its production is disclosed in U.S. Pat. No. 4,952,716 and U.S. Pat. No. 5,227,507. Synthetic zeaxanthin is commercially available from DSM, who purchased the technology from Hoffmann-LaRoche. Hoffmann-LaRoche had obtained two patents that describe the chemical synthesis of the 3R,3'R isomer of zeaxanthin; these are U.S. Pat. No. 4,952,716 and U.S. Pat. No. 5,227,507. Processes disclosed therein require the production and purification of three major intermediates, with yields of approximately 70 to 85% for each intermediate from its precursor. The overall process disclosed in these patents apparently requires a series of 14 reaction steps, which take a minimum of 83 hours (excluding purification), and yield a mixture of reactants and products. The final reaction mixture must then be extensively treated to purify the 3R,3'R isomer of zeaxanthin. Accordingly, the entire process required for both synthesis and purification using this technique makes production on a commercial scale overly difficult, and expensive. The zeaxanthin produced synthetically is currently available only in the non-esterified form. A significant problem with certain synthetically derived carotenoids is elevated levels of residual solvents (used in their synthesis) that typically remain in and contaminate the final product. For example, commercial synthetic beta-carotene was analyzed in our laboratory and shown to contain residual levels of toluene or acetone, of 2000 and 1200 ppm, respectively, depending on the synthetic source. These levels, generally unknown to the public, are undesirable, and are roughly 50 to 100 times higher than levels of residual solvents permitted under 21 CFR §173 for spice extractives containing high levels of carotenoids, such as paprika or carrot oleoresin.

Plant Sources of Zeaxanthin

The public generally prefers to consume compounds that are derived from natural sources as opposed to those that are produced synthetically. Natural sources containing high levels of zeaxanthin currently include certain mutant varieties of marigold flower petals, berries of the genus *Lycium* and *Physalis*, and specifically Chinese wolfberries (*Lycium chinense*). U.S. Pat. No. 6,191,293 discloses that preferred materials containing zeaxanthin "include fruits like oranges, peaches, papayas, prunes, and mangos." There is no mention in this patent of the genus *Capsicum*.

Marigolds

Marigold (*Tagetes erecta*) petals have a long history as a commercial source of the carotenoid pigment, lutein. Dried marigold flowers contain approximately 1-1.6% carotenoids by weight and lutein esters generally account for 90% of the total carotenoids (Antony et al., 2001). U.S. Pat. No. 6,784, 351 discloses a mutant marigold that expresses zeaxanthin at high levels, where zeaxanthin is the dominant carotenoid pigment. Marigold petals, however, are not a recognized food. Although lutein derived from marigolds has been introduced as a food additive through the use of the self-affirmed GRAS (Generally Recognized as Safe) process, it cannot be added to foods if it changes the food's color. This is because lutein is not recognized as an exempt food colorant under 21 CFR §73.

There is another problem associated with pigments isolated from marigolds. Marigolds are often planted around gardens because they naturally produce insecticidal compounds and when planted in proximity to other plants, help shield them from insect predation. One type of these natural insecticides is a group of compounds known as terthiophenes and related compounds. Terthiophenes are potent phototoxic agents that cause light-activated damage to biological systems [Downum et al., (1995); Aranson, et al., (1995)]. These phototoxic compounds can be difficult to separate from marigold-derived zeaxanthin. Analysis of commercially available zeaxanthin (and lutein) from marigold sources demonstrates that such preparations contain measurable levels of phototoxic terthiophenes (see Example 12). Therefore, marigold-derived zeaxanthin is certainly not a preferred form for eye health. α-Terthiophene (also known as α-terthienyl) and other marigold constituents, such as butenylbithiophene and hydroxytremetone have been reported to have sensitizing properties leading to allergic contact dermatitis [Hausen et al, (1995)]. The zeaxanthin-containing extracts of the present *Capsicum* varieties do not contain these sensitizing or photosensitizing components.

Conversion of Marigold-Derived Lutein to Zeaxanthin

Lutein to zeaxanthin isomerization reactions have been known for more than 40 years. One process disclosed in, U.S. Pat. No. 6,376,722 uses sodium ethoxide, methanol, potassium methoxide, methyl sulfate, and combinations thereof to effect this conversion.

The weaknesses of this approach are 1) that zeaxanthin derived from marigolds is not GRAS for food and 2) that phototoxic compounds derived from marigold are not necessarily removed. Additionally, the extra reaction step is also expensive and lowers the yield of zeaxanthin obtained.

Wolfberries

High concentrations of the dipalmitate ester of zeaxanthin have been isolated from wolfberries (*Lycium chinense*) which have a history of use in Chinese medicine, Zhou et al., (1999). Since they are not a GRAS food substance, according to 21 CFR 182, the potential use of wolfberries in food systems is limited.

Fruit and Vegetable Crops

Zeaxanthin is found in a wide variety of fruits and vegetables as shown in Table 1 (Lutein and Zeaxanthin Scientific Review, Roche Vitamins Technical Publication HHN-1382/0800). These levels are quite low compared to the concentrations present in the instant invention [about 60,000 micrograms/100 g on a raw (wet) basis].

TABLE 1

Concentration of zeaxanthin in commonly consumed fruits and vegetables.

| | | |
|---|---|---|
| Tangerine, mandarin | 142 microgram/100 g | 0.000142% |
| Kale (cooked) | 173 microgram/100 g | 0.000173% |
| Spinach (cooked) | 179 microgram/100 g | 0.000179% |
| Lettuce (cos or romaine, raw) | 187 microgram/100 g | 0.000187% |
| Collard greens (cooked) | 266 microgram/100 g | 0.000266% |
| Turnip greens (cooked) | 267 microgram/100 g | 0.000267% |
| Spinach (raw) | 331 microgram/100 g | 0.000331% |
| Corn (frozen, cooked) | 375 microgram/100 g | 0.000375% |
| Persimmons (Japanese, raw) | 488 microgram/100 g | 0.000488% |
| Corn (sweet, yellow, cooked) | 528 microgram/100 g | 0.000528% |
| Pepper (orange, raw) | 1606 microgram/100 g | 0.001606% |

*Capsicum*

There are two principle types of *Capsicum annuum* which have a very low capsaicin content: bell and paprika types. The presence or absence of capsaicin, the pungent principle in peppers, is not critical to this invention, as some paprikas are perceptibly hot.

Three major pigment type classes of paprika-type peppers are discussed, which are herein referred to as reds, oranges, and yellows. Red, orange and yellow fruit of the *Capsicum* genus are generally good dietary sources of carotenoids. The pepper referred to in Table 1. is a *Capsicum*. The appearance of a given class is determined by the relative amounts of the pigments in combination with the total pigment concentration. Regardless of the total concentration, and visual appearance, these classes can be differentiated by spectral analysis, and by HPLC. For example, a pod from a red paprika will appear orange if it has a low pigment concentration, but has a visible spectrum and HPLC analysis different from the instant orange paprika exhibiting a high zeaxanthin content. In a red paprika, substantial amounts of the red pigments capsorubin and capsanthin are present. In the orange paprika, a minor amount of these two pigments are present, and a very high concentration of zeaxanthin is present. In yellows, the two red pigments are absent as well as a precursor, violaxanthin. Lutein and other yellow pigments and their precursors are present at significantly higher ratios to zeaxanthin, and total pigment content is much lower as shown by a much lower ASTA value.

Table 2. summarizes the concentration of zeaxanthin and the percentage of zeaxanthin relative to total carotenoids in dried *Capsicum* fruits which have been reported in the literature. Table 2 shows that the percent zeaxanthin with respect to the total carotenoids in the *Capsicum*, as well as the weight percent of zeaxanthin as a percent of dry weight of the fruit, are much lower than the surprisingly high amounts of zeaxanthin which is characteristic of the instant invention.

TABLE 2

Content and ratios of zeaxanthin in prior art *Capsicum* varieties (dry weight).

| Zeaxanthin as % of total carotenoids | Zeaxanthin as % of dry fruit weight | Reference |
|---|---|---|
| 9.15 | 0.045 | Matus et al., (1991) |
| 3.83 | 0.06 | Almela et al., (1991) |
| 2.91 | 0.043 | " |
| 4.35 | 0.058 | " |
| 2.07 | 0.026 | " |
| 4.32 | 0.053 | " |
| 2.73 | 0.027 | " |
| 4.26 | 0.034 | " |
| 8.49 | 0.273 | Deli et al., (1992) |
| | 0.009 | Minguez-Mosquera et al., (1993) |
| | 0.03 | " |
| 16.2 | 0.161 | Deli et al., (1996) |
| 17.9 | 0.109 | " |
| 20.5 | 0.027 | " |
| 4.1 | 0.033 | Almela et al., (1996) |
| 3.3 | 0.044 | " |
| 14.2 | 0.019 | Topuz et al., (2003) |
| 13 | 0.013 | " |
| 6.3 | 0.081 | Hornero-Mendez et al., (2002) |
| 6 | 0.045 | " |
| 8.5 | 0.064 | " |
| 8.2 | 0.056 | " |
| 7 | 0.068 | " |
| 6.9 | 0.072 | " |
| 8.4 | 0.041 | " |
| 14 | 0.135 | " |
| 14.9 | 0.165 | " |
| 7.7 | 0.074 | " |
| 9 | 0.073 | " |
| 8.4 | 0.081 | " |
| 8.1 | 0.049 | Deli et al., (1997) |
| 17.5 | 0.0952 | Deli et al., (2001) |
| 8.8 | 0.1145 | " |
| 6.2 | 0.0312 | Minguez-Mosquera et al., (1994) |
| 10.9 | 0.073 | " |
| 7.2 | 0.028 | Muller, H. (1997) |
| 3.1 | 0.006 | Camara et al. (1978) |
| 7.9 | 0.134 | Minguez-Mosquera et al (1993) |
| 4.6 | 0.055 | Minguez-Mosquera et al (1993) |
| 5.2 | 0.064 | Minguez-Mosquera et al (1994) |
| 9.2 | 0.045 | Biacs et al. (1993) |
| 11.3 | 0.103 | Rahman et al (1980) |

TABLE 2-continued

Content and ratios of zeaxanthin in prior art *Capsicum* varieties (dry weight).

| Zeaxanthin as % of total carotenoids | Zeaxanthin as % of dry fruit weight | Reference |
| --- | --- | --- |
| 8.9 | 0.023 | Rahman et al (1980) |
| 8.1 | 0.02 | Rahman et al (1980) |
| 9.2 | 0.02 | Rahman et al (1980) |
| 5.28 | 0.024 | Biacs, P. A. et al., (1994). |
| 4.5 | | Deruere, J., etal. (1994). |
| 2.3 | | Nys, Y. et al., (2000) |
| 2.3 | | Fisher, C. et al., (1987) |
| 6.5 | | Nys, Y. et al., (2000) |
| 6.5 | | Fisher, C. et al., (1987) |
| 3.1 | | Nys, Y. et al., (2000) |
| 3.1 | | Fisher, C. and Kocis, J. A. J. Agric. Food Chem. 1987, 35, 55-57. |
| 4 | | Nys, Y. et al., (2000) |
| 4 | | Fisher, C. et al., (1987) |
| 15.67 | 0.0201 | Russo, V. M. et al., (2002) |
| 11.27 | 0.0397 | Russo, V. M. et al., (2002) |

Indeed, this fact has been stated by, Breithaupt et al. (2005), who observed "additionally, oleoresins containing zeaxanthin as sole or even major xanthophyll are not available." One of the highest amounts or levels of zeaxanthin which has been previously described for *Capsicum* varieties or cultivars is found in the *longum nigrum* variety as reported by Deli et al., (1992). This variety contains about 0.273% zeaxanthin in the dried, ripe fruit pod flesh. However, the percent ratio of zeaxanthin to total carotenoids in this *longum nigrum* variety is only 8.49%. Varieties with somewhat higher ratios of zeaxanthin relative to total carotenoids have been described. The *lycospersiciforme rubrum* varieties described by Deli et al., (1996), show percent ratios of zeaxanthin to total carotenoids of 16.2%, 17.9% and 20.5%; however, the mass of zeaxanthin present in dried, ripe fruit pod flesh is much lower in these varieties, 0.027%, 0.109% and 0.161% of the total dried ripe fruit pod flesh, respectively.

There are reports in the literature on the analysis of carotenoids in fresh *Capsicum* fruit. The use of fresh versus dehydrated fruit introduces a complicating factor into estimating the amount of zeaxanthin in the fresh fruit for comparison with that amount found in dried fruit (as reported in Table 2). Breithaupt et al., (2001) have found that an orange pepper (*Capsicum annuum* L. Grossum Grp.) contains 9234 micrograms of total carotenoids per 100 grams of fresh fruit pod flesh. The results were reported as lutein dimyristate equivalents, and neither the absolute nor relative amounts of zeaxanthin were reported. Most paprika-type peppers have a moisture content of 80-85%. Succulent varieties (e.g. bell peppers) have been reported to contain up to 92% moisture (Banaras et al., 1994). Applying assumptions in this case to skew the results toward high zeaxanthin content, specifically, that this pepper was a bell pepper with 92% moisture, and, unrealistically, that zeaxanthin made up all the carotenoids present, the *Capsicum* sample in question would contain only 0.12% zeaxanthin. Weller et al., 2003, found 3.03 milligrams of zeaxanthin per 100 grams of a fresh orange pepper (*Capsicum annuum* L.). Using the previous 92% water content assumption, this calculates to 0.04% zeaxanthin on a dry-weight basis. The ratio of zeaxanthin to total carotenoids reported by Weller et al. for this particular pepper was 44%. These authors also describe a red pepper with 16.75 mg of zeaxanthin per 100 g of fresh fruit. Using the same, unrealistic assumption, that this is a bell pepper with 92% water content, this calculates to a 0.21% zeaxanthin. The ratio of zeaxanthin to total carotenoids for this red pepper is only 15%.

Abellan-Palazon, et al., 2001, reported a paprika cultivar treated with titanium ascorbate to have 0.56% zeaxanthin, however, the percentage of zeaxanthin relative to other carotenoids was only 16.6% for this cultivar. The water content of this fresh pepper was given as 79.9% and this was the factor used for the moisture correction. Abellan-Palazon, et al. also reported that after drying this sample, the mass percent zeaxanthin fell to 0.16% and the percentage of zeaxanthin relative to other carotenoids fell to 8.4%. Sommerburg, et al., 1998, report that orange pepper was the vegetable with the highest amount of zeaxanthin with 37 mole percent. Adjusting for molecular weights, this calculates to ~37.8% by weight, well below the >50% reported in the instant invention. Sommerburg's data do not allow calculation of the mass percent zeaxanthin in the orange pepper from the mole percent data.

Bacterial Sources of Zeaxanthin

Bacteria provide another source of zeaxanthin as in U.S. Pat. No. RE 38,009, which discloses a method to produce zeaxanthin by a fermentation process with *Flavobacterium multivorum* (ATCC 55238). Other bacteria have been identified that can express zeaxanthin, and they include microbes from the genus *Flavobacter* (ATCC 21081, 21588, and 11947). Zeaxanthin from a bacterial source is not GRAS. Furthermore, the safety of extracts from bacteria is not established. No commercial source of bacterially derived zeaxanthin is known to be available.

OBJECTS OF THE INVENTION

It is an object of the present invention to provide novel *Capsicum* genus plants, or regenerable portions thereof, which plants produce fruit pods which exhibit in their dried, ripe flesh a hyper-accumulation of carotenoid pigment, wherein zeaxanthin is a mixture of free zeaxanthin and fatty acid esters, and is the dominant carotenoid when measured in non-esterified forms.

It is an object of the present invention to provide novel *Capsicum* genus plants, or regenerable portions thereof, which plants produce fruit pods which exhibit in their dried, ripe flesh a hyper-accumulation of carotenoid pigment, wherein zeaxanthin, measured as free diol, is present at greater than about 0.4% by weight of the dry, ripe fruit pod flesh.

It is an object of the present invention to provide novel and commercially viable strains of *Capsicum annuum* paprika type plants, which plant produces orange-colored fruit pods and which plant exhibits in the dried ripe fruit pod flesh, carotenoid pigments with an ASTA value of greater than 175, wherein zeaxanthin is the dominant carotenoid.

An additional object of the invention is the provision of *Capsicum* products/compositions derived from such plants.

An additional object of the invention is the provision of processes for developing such plants, extracting *Capsicum* products from the ripe pod flesh of such plants and methods of treating various conditions with products derived from such plants.

DESCRIPTION OF THE INVENTION

What we therefore believe to be comprised by our invention may be summarized inter alia in the following words: *Capsicum* variants developed through a selective breeding process which express high absolute and relative levels (compared to total carotenoids when measured in non-esterified forms) of zeaxanthin, as a mixture of free zeaxanthin and fatty acid esters of zeaxanthin. The invention relates to *Capsicum* plants, regenerable portions thereof, hybrids or later generations, wherein the dried, ripe fruit pod flesh thereof exhibits a level of zeaxanthin, as a percentage of dry, ripe fruit pod flesh weight, which is greater than 0.4% measured as total non-esterified zeaxanthin following a saponification process. The invention further relates to *Capsicum* plants, regenerable portions thereof, hybrids or later generations, wherein the dried, ripe fruit pod flesh thereof exhibits a percentage of zeaxanthin relative to total carotenoids [mass zeaxanthin/(mass zeaxanthin plus mass of other carotenoids)×100] which is greater than 50% when measured in non-esterified forms. The invention further relates to strains of *Capsicum annuum* paprika type plants, which plant produces orange-colored fruit pods and which plant exhibits in the dried ripe fruit pod flesh, carotenoid pigments with an ASTA value of greater than 175, and by the predominance of zeaxanthin.

BRIEF DESCRIPTION OF THE INVENTION

A plant, or regenerable portion thereof, of the *Capsicum* genus, which plant produces fruit pods and which plant exhibits in the dried ripe fruit pod flesh, a hyper-accumulation of carotenoid pigment, wherein zeaxanthin is the dominant carotenoid, when measured in non-esterified forms, such a plant, or regenerable portion thereof, which is a member of the species *annuum*, such a plant, or regenerable portion thereof, which is a paprika variety, such a plant, or regenerable portion thereof, wherein the mass of zeaxanthin, when measured in non-esterified form, is greater than 0.4% of the total dried ripe fruit pod flesh, such a plant, or regenerable portion thereof, wherein the percentage of zeaxanthin relative to total carotenoids in the dried ripe fruit pod flesh is greater than 50%, such a plant, or regenerable portion thereof, wherein the mass of zeaxanthin is greater than 0.4% of the total dried ripe fruit pod flesh, such a plant, or regenerable portion thereof, of the *Capsicum* genus which plant produces fruit pods and which plant exhibits in the dried ripe fruit pod flesh, zeaxanthin, and wherein the mass of zeaxanthin, when measured in non-esterified form, is greater than 0.6% of the total dried ripe fruit pod flesh, such a plant, or regenerable portion thereof, wherein the mass of zeaxanthin is greater than 0.7% of the total dried ripe fruit pod flesh, such a.

plant, or regenerable portion thereof, wherein the mass of zeaxanthin is greater than 0.8% of the total dried ripe fruit pod flesh, such a plant, or regenerable portion thereof, wherein the mass of zeaxanthin is greater than 0.9% of the total dried ripe fruit pod flesh, such a plant, or regenerable portion thereof, which plant exhibits in the dried ripe fruit pod flesh, an ASTA value greater than 175, wherein zeaxanthin is present at a level of greater than about 50% of the HPLC area count of the total pigments, such a plant, or regenerable portion thereof, which plant exhibits in the dried ripe fruit pod flesh, an ASTA value greater than 200, such a plant, or regenerable portion thereof, which plant exhibits in the dried ripe fruit pod flesh, an ASTA value greater than 225, such a plant, or regenerable portion thereof, which plant exhibits in the dried ripe fruit pod flesh, an ASTA value greater than 275, such a plant, or regenerable portion thereof, wherein the mass of zeaxanthin is greater than 0.4% of the total dried ripe fruit pod flesh, such a plant, or regenerable portion thereof, characterized by a capsanthin plus capsorubin content of less than about 10% of the HPLC area count of total pigments, such a plant, or regenerable portion thereof, characterized by a capsanthin plus capsorubin content of less than about 7% of the HPLC area count of total pigments, such a plant, or regenerable portion thereof, characterized by a zeaxanthin content of greater than about 60% of the HPLC area count of total pigments, such a plant, or regenerable portion thereof, characterized by a zeaxanthin content of greater than about 70% of the HPLC area count of total pigments, such a an oleoresin composition derived from the plant, or regenerable portion thereof, such a plant, or regenerable portion thereof, wherein the regenerable portion is selected from the group consisting of embryos, meristems, pollen, leaves, anthers, ovules, roots, root tips, fruit pods, seeds, petals, flowers, fibers, bolls, and protoplasts or callus derived therefrom, such a cell culture or tissue culture of the plant, or regenerable portion thereof, such a grafted plant or progeny of the regenerable portion, such a seed, which on planting in a suitable environment and grown to maturity yields a plant of the *Capsicum* genus, such a hybrid *Capsicum* plant, wherein one ancestor is a *Capsicum* variety, such a genome of the plant, or regenerable portion thereof, such a plant extract composition comprising zeaxanthin derived from the *Capsicum* plant, or regenerable portion thereof, such a plant extract composition which is an ingredient in cosmetics and cleaning preparations selected from lipsticks, lotions, soaps, foundations, mascara, eye shadow, body scrubs, sun lotion, muds, packs, masks, shampoos, conditioners and toothpastes, such a plant extract composition which is an ingredient in animal feed supplements, such a plant extract composition which is an ingredient in foods and beverages, such a plant extract composition which is a colorant in foods, beverages, and animal feed, such a plant extract composition wherein the zeaxanthin is in the form of mono-esters, di-esters, the free alcohol form, or a combination thereof, such a plant extract composition wherein the zeaxanthin is an all trans geometric isomer, or cis geometric isomers or combinations thereof, such a plant extract composition in the form of a solid or a semi-solid, such a plant extract composition wherein the form is selected from powders, beadlets, water-dispersible powders, crystals, amorphous solids, and encapsulated solids, such a plant extract composition in the form of an emulsion, such a plant extract composition in an ingestible form selected from capsules, tablets, beadlets, titration packs, powders, drops, lozenges, sprays, syrups, rapidly dissolvable strips and time release capsules, such a plant extract composition in a non-ingestible form selected from dermal patches, injectable solutions, drops, suppositories, topical lotions, creams, and sprays, such a plant extract composition further comprising extracts of *Labiatae* herbs (including rosemary, sage, oregano, peppermint, basil, spearmint, summer savory), olive extracts, coffee extracts, citrus extracts, tea extracts, tea catechins, catechin, epi-catechin, epi-catechin gallate, epi-gallocatechin gallate, gallic acid, tocopherols, tocotrienols, ascorbic acid and ascorbates (including ascorbyl palmatate), erythorbic acid and erythorbates, glutathione, carnosic acid, carnosol, rosmanol, rosmarinic acid, salviaflaside, flavonoids or flavonoid glucuronides (including quercitin, luteolin, apigenin, or glucuronides of quercitin luteolin, and apigenin and the like), curcumin, tetrahydrocurcumin, hydroxy tyrosol, oleuropein, BHT, BHA, hydroxylamines, propyl gallate, ethoxyquin, Trolox or TBHQ, or mixtures thereof, such a plant extract composition further comprising extracts of *Bixa orellana, Curcuma longa, Daucus carota sativa, Capsicum annuum* (other than the inventive plant), *Dunaliella salina, Haematacoccus pluvalus*, beta-carotene, beta-apo-8-carotenal, the ethyl ester of the beta-apo-8-carotenoic acid, synthetic colors (FD&C coloring agents), and/or mixtures thereof, such a plant extract composition which is ingested for human and animal eye health and/or to reduce the risk of developing ocular diseases including cataracts, age-related macular degeneration, Retinitis Pigmentosa, Usher syndrome, Stargardts, Best's Disease, progressive Cone Dystrophy and retinal degradation, such a plant extract composition which is ingested for the treatment or the prevention of human or animal diseases including cancer-related diseases, cardiovascular diseases, inflammatory disorders and nervous system diseases, such a plant extract composition wherein the cancer-related diseases are selected from breast cancer, gastric cancer and melanoma, such a plant extract composition wherein the inflammatory disorder is selected from polyarthritis and rheumatoid arthritis, such an oleoresin composition derived from the plant or regenerable portion thereof, such an oleoresin composition comprising zeaxanthin, cryptoxanthin, lutein, and other carotenoids, such an oleoresin composition wherein the oleoresin is substantially free from terthiophenes, such an oleoresin composition wherein the oleoresin meets the requirements of 21 CFR §73 regulations for spice extractives, such a presscake derived from the plant, such a fresh or dried fruit of the plant in either the whole or comminuted form, such saponified products derived from the plant, such seasoning and flavoring compositions derived from the plant, comprising natural flavors and synthetic flavors, such pigmenting, flavoring, and/or preserving compositions derived from the plant for animal and human foods, such a method for the prevention of degenerative or free radical-mediated diseases including age-related macular degeneration, cataracts, cardiovascular disease and cancer, comprising the step of administering to a living animal body, including a human, zeaxanthin derived from the plant, or regenerable portion thereof, in a nutritionally effective amount for the prevention of such diseases, such a method for the treatment of degenerative or free radical-mediated diseases including age-related macular degeneration, cataracts, cardiovascular disease and cancer, comprising the step of administering to a living animal body, including a human, zeaxanthin derived from the plant, or regenerable portion thereof, in an amount effective to provide a therapeutic benefit to the subject suffering from such diseases, such a method for reducing the risk of developing ocular disorders selected from cataracts, retinal degeneration, age-related macular degeneration, Stargardts, Best's Disease, progressive Cone Dystrophy, Retinitis Pigmentosa, Choroideremia, Ushers Syndrome and Diabetic Retinopathy, comprising the step of administering to a living animal body, including a human, zeaxanthin derived from the plant, such a method for reducing the risk of developing free radical-mediated diseases selected from cancer-related diseases, cardiovascular diseases, inflammatory disorders, nervous system diseases, comprising the step of administering to a living animal body, including a human, zeaxanthin derived from the plant, such a method wherein the cancer-related diseases are selected from breast cancer, gastric cancer and melanoma, such a method wherein the inflammatory disorders are selected from polyarthritis and rheumatoid arthritis, such a method for pigmenting, flavoring, and/or preserving animal and human foods comprising the step of incorporating an extract composition derived from the plant, or regenerable portion thereof, into the animal and human foods, such a method for pigmenting, flavoring, and/or preserving animal and human foods comprising the step of incorporating zeaxanthin derived from the plant, or regenerable portion thereof, into the animal and human foods, such a method of obtaining a non-esterified zeaxanthin of high purity comprising:
(a) contacting ground ripe fruit pods from the plant, or regenerable portion thereof, of claim 1 with a solvent for a time sufficient to extract zeaxanthin from the fruit pods;
(b) separating the solvent and extract dissolved therein from the remaining plant material;
(c) desolventizing the extract to obtain a zeaxanthin oleoresin;
(d) refluxing the zeaxanthin extract in the dark with butylated hydroxytoluene, sodium carbonate and potassium hydroxide to lower the pH; and
(e) neutralizing the solution to produce a solution of pure non-esterified zeaxanthin.

DETAILED DESCRIPTION OF THE INVENTION

Figure 1:
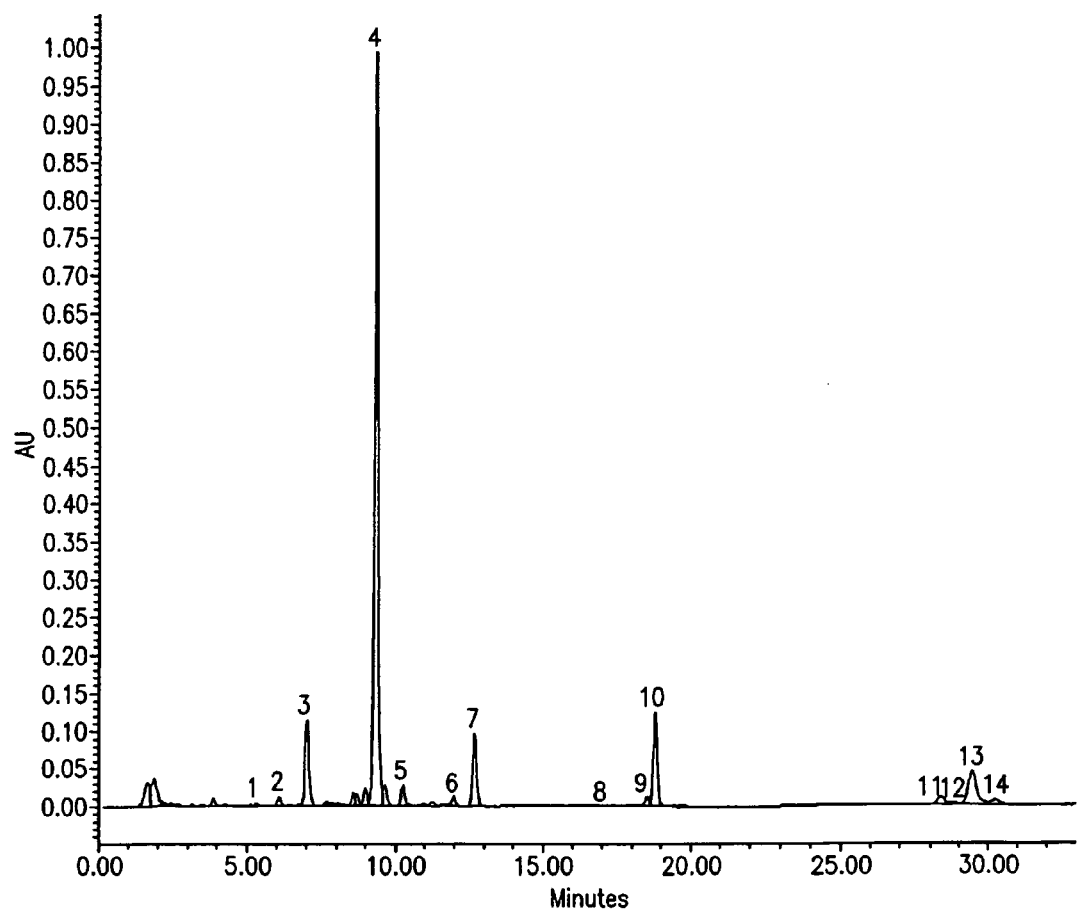
FIG. 1 is an HPLC chromatogram (maxplot 400 nm-600 nm) as set forth in Example 8, of saponified oleoresin derived from the instant *Capsicum* varieties. Peak identification is as follows: 1=capsorubin, 2=violoxanthin, 3=capsanthin, 4=trans-zeaxanthin, 5=lutein, 6=antheraxanthin, 7=9-cis-zeaxanthin, 8=cryptocapsin, 9=α-crytpoxanthin, 10=β-cryptoxanthin, 11=ζ-carotene, 12=α-carotene, 13=trans-β-carotene and 14=cis-β-Carotene. Ratios of zeaxanthin to total carotenoids were calculated by summing the area counts for all the zeaxanthin isomers and dividing that number by the total area count of all the carotenoid peaks.

For the purpose of this invention, the term zeaxanthin includes zeaxanthin in all of its geometrically isomeric, stereoisomeric and derivatized forms. Lutein is not regarded herein as an isomer of zeaxanthin. Zeaxanthin geometric isomers include the all-trans form as well as the various cis isomers such as 9-cis, 13-cis, and 15-cis. The stereoisomeric forms include 3R,3'R; 3S,3'R; 3R,3'S and 3S,3'S. The derivatives of zeaxanthin include both the free hydroxyl form as well as esters with various fatty acids that are typically known to occur in the art. The invention applies to combinations of all these forms of zeaxanthin. The plants of the instant invention produce predominately trans 3R,3'R as a mixture of free hydroxyl compounds and mono- and di-esters of fatty acids.

The *Capsicum* genus includes all species and varieties known in the art and that could be developed. These species include but are not limited to *annuum, frutescens, pubescens, chinense.*

The instant invention pertains to *Capsicum* varieties exhibiting a hyper-accumulation of zeaxanthin which are derived through mass selection, seed to row evaluation, single plant selection breeding techniques, or other techniques known in the art. These techniques are used to produce plants having the following characteristics:

1. The mass of zeaxanthin in the dried ripe fruit pod flesh, measured as the free or non-esterified diol, is greater than about 0.4% of the mass of total dried, ripe fruit pod flesh.
2. The percentage of zeaxanthin relative to total carotenoids present in the dried, ripe fruit pod flesh, when measured in the non-esterified forms, is the dominant carotenoid, defined as the carotenoid present in the highest concentration, or is greater than about 50%. The total carotenoids are defined as their free forms in those cases where esterification is possible. Examples are capsanthin and cryptoxanthin.
3. The mass of zeaxanthin relative to other characteristic carotenoids present in the dried, ripe fruit pod flesh in highly pigmented varieties is 4- to 5-fold greater in the instant orange varieties when compared with commercial red varieties.

Hyper-accumulation is a term open to interpretation. In the context of this document, a plant exhibiting a hyper-accumulation of zeaxanthin is one which expresses an amount about twenty-fold higher than the amount exhibited by a standard orange pepper, as defined in Table 1, as providing 1606 microgram zeaxanthin per 100 gram of raw pepper flesh. Assuming a 92% moisture level in the raw pepper, the weight of zeaxanthin for this standard pepper would be 0.02% on a dry weight basis. A pepper exhibiting hyper-accumulation would then contain about 0.4% zeaxanthin in the dry, ripe fruit pod flesh.

As used herein the term dried refers to a range of moisture contents typically observed when paprika is dehydrated. The drying can occur by any means known in the art, including sun drying, oven drying and freeze drying. Moisture contents in dried paprika can range from 1 to 20% by weight, however, typical ranges are between 2 and 10%.

As used herein the flesh of the fruit pod may or may not include the pulp, seeds, stem, placenta, and pericarp.

As used herein the phrase "tissue culture" refers to plant cells or plant parts from which *Capsicum* plants or plant cultures may be generated, including plant protoplasts, plant cali, plant clumps, and plant cells that are intact in plants, or part of plants, such as seeds, leaves, stems, pollens, roots, root tips, anthers, ovules, petals, flowers, embryos, fibers and bolls.

Techniques of generating plant tissue culture and regenerating plants from tissue culture are well known in the art. For example, such techniques are set forth by Vasil., 1984, Green et al., 1987, Weissbach et al., 1989, Gelvin et al., 1990, Evans et al., 1983, and Klee et al., 1987.

Tissue culture of plant cells or plant parts may be generated from plant protoplasts, plant cali, plant clumps, and plant cells that are intact in plants, or parts of plants, which when regenerated, produce plants or plant material capable of expressing the morphological and/or physiological characteristics of the instant *Capsicum* plants.

Regenerable portions of the *Capsicum* plants of the present invention, derived from plant cells or protoplasts of a tissue selected from the group consisting of embryos, meristems, pollen, leaves, anthers, ovules, roots, root tips, fruit pods, seeds, petals and flowers, fibers and bolls, may be cultured to produce plants or plant material capable of expressing all the physiological characteristics of the instant *Capsicum* varieties, including a hyper-accumulation of zeaxanthin.

Subcellular constituents of the regenerable cells, comprising nucleic acids, polypeptides and carotenoids, may be isolated from plant cells or protoplasts of the instant *Capsicum* plants.

The invention also pertains to the genetic sequences and corresponding amino acid sequences which govern and make possible the hyper-expression and/or accumulation of zeaxanthin characteristic of the instant *Capsicum* varieties.

The nucleic acids of the instant invention may be used to create transgenic plants or organisms in which the levels of zeaxanthin are present at higher than normal levels. To this end, it may be desirable to reduce or eliminate expression of genes encoding carotenoid biosynthetic enzymes in plants, including capsanthin-capsorubin synthase or zeaxanthin epoxidase, which downregulation may result in a hyper-accumulation of a carotenoid precursor. Advances in genetic engineering have provided the requisite tools to transform plants to contain and express foreign genes (Kahl et al., 1995; Hodges, et al. U.S. Pat. No. 5,527,695; Conner, et al., U.S. Pat. No. 6,506,565), as well as tools to silence the expression of genes in plants through antisense technologies (Shewmaker, et al. U.S. Pat. No. 5,107,065). The limitations of conventional plant breeding may be circumvented by the creation of transgenic plants genetically engineered to express a desired phenotype (Yin, et al., 2004, and references therein). Therefore, a variety of strategies and molecular techniques can be used by a skilled artisan to increase the amount of carotenoids in a plant. For example, to increase the level of zeaxanthin in plants, molecular techniques may be used to transform wild type plants with the instant nucleic acids according to conventional methods in the art to alter the activity of enzymes of the carotenoid biosynthetic pathway in those plants which result is the hyper-accumulation of zeaxanthin.

Breeding

Plants of the instant invention are of the genus *Capsicum* and are the product of a plant breeding program using classical plant breeding methods of hybridization, single plant selection and progeny row evaluation.

Seed or Plant Treatment

Alterations in carotenoid biosynthesis, including enhanced production of zeaxanthin, could lead to changes in the amount or timing of abscisic acid production in the plants of the present invention. It may be necessary to treat the plants or seeds with abscisic acid or abscisic acid precursors or other treatments known in the art at some point in their development in order to avoid adverse impacts on germination, germination rate or germination timing. Such treatment is known in the art for a wide variety of plants.

Harvesting

Fruit pods produced by plants of the present invention can be harvested by any means known in the art. The preferred method to harvest the *Capsicum* species of interest is mechanical. Manual harvesting may also be used. The fruit pods can be harvested in their fully hydrated form, providing, a pepper for the fresh produce market. The fruit pods can also be harvested in a partially desiccated state, after the pods have dried down on the plant in the field (see examples).

Dehydration

Fresh or partially desiccated pods can be further dried by any means known in the art, including sun drying, oven drying, freeze drying and the like.

Grinding

Desiccated pods can be comminuted or ground by methods known in the art.

Method of Extraction

Zeaxanthin and other carotenoids may be obtained by extraction of the fresh pod flesh, by extraction of the dried fruit, or by extraction of a mixture thereof. In some cases, it is preferred to grind the pod flesh into either a paste or a powder prior to the extraction process. The grind profile can be optimized by means known in the art. Extraction can be done using any of the methods currently known in the art. These include, but are not limited to extraction with a solvent, or a mixture of solvents, such as those approved under 21 CFR §173, extraction by mechanical means using a press, such as described in U.S. Pat. No. 5,773,075, extraction with subcritical or supercritical fluids, such as supercritical carbon dioxide in the presence or absence of additional solvents or co-solvents, extraction with hydrocarbons, such as ethane, propane or butane, extraction with hydrofluorocarbons, such as tetrafluoroethane or with tetrafluoroethane mixed with those organic solvents approved under 21 CFR §173. Suitable solvents for extraction include, but are not limited to n-hexane, cyclohexane, branched hexanes, heptane, branched heptanes, octane, nonane, decane, and other hydrocarbons. Suitable solvents also include, but are not limited to ethyl acetate, tetrahydrofuran, methyl-tert-butyl-ether, ethanol, methanol, acetone, limonene, and other essential oils. As known by those skilled in the art, combinations of these solvents can also be utilized for the extraction. Those methods that involve the use of a solvent are generally followed by a desolventizing process, including, but not limited to distillation, vacuum distillation, steam distillation, evaporation, steam stripping, nitrogen stripping, membrane pervaporation, or molecular distillation.

Further Processing

Whole fresh pods, dried pods, ground pods, or extracts of pods of the instant *Capsicum* varieties can be heated to convert all or a portion of the naturally occurring all-trans zeaxanthin into cis forms. In a similar manner, whole fresh pods, dried pods, ground pods, or extracts of pods of the instant *Capsicum* varieties can be irradiated with light of wavelength sufficient to convert all or a portion of the naturally occurring all-trans zeaxanthin into similar or additional cis forms. Alternatively, the cis forms of zeaxanthin can be converted back into trans forms by refluxing in ethanol (Khachik et al. 1992), Other carotenoids such as beta carotene and beta-apo-8-carotenal have also been shown to convert from cis to the all trans form in high yield by heating in petroleum ether or water followed by crystallization (Isler, et al. 1956; U.S. Pat. No. 3,989,757 and references therein). Other chemical means known in the art may be used to interconvert cis and trans isomers.

Ground, dried, pod flesh of the *Capsicum* of the present invention can be treated with caustic solution or with enzymes to saponify or hydrolyze the zeaxanthin and other carotenoids present in esterified form, together with any other hydrolysable material [see U.S. Pat. No. 5,648,564]. The free zeaxanthin and other carotenoids can be separated from the hydrolysate by means known in the art, including dissolving the free zeaxanthin and other carotenoids in a suitable solvent, filtering or otherwise separating insoluble components from the solvent/zeaxanthin/other carotenoid mixture, and separation of the solvent from the zeaxanthin/other carotenoid mixture.

Alternatively, the ground material may be transesterified, using methods known in the art, reacting fatty acids with the zeaxanthin (and other xanthophylls) in order to make a preferred esterified form of zeaxanthin and other xanthophylls.

Further Forms or Formulations of Zeaxanthin

This invention pertains to forms and formulations of zeaxanthin derived from *Capsicum* varieties, those plants exhibiting a percent of zeaxanthin relative to total carotenoids which is greater than 50% in the dried, ripe fruit pod flesh, when measured in non-esterified forms. Such forms and formulations are designed and intended for consumption by humans and animals as nutritional supplements, as food colorants or additives, for the fortification of human food or animal feeds, or as ingredients in cosmetic, personal care or pharmaceutical applications.

Fresh Pepper

The plant product may take the form of the fresh fruit pods harvested from a *Capsicum* plant, in whole, comminuted, pureed, macerated or expressed juice form.

Dehydrated Pepper

The plant product may take the form of the dehydrated, dried, or desiccated fruit pods harvested from a *Capsicum* plant, in whole, comminuted or ground form. These dehydrated pepper products could reach the consumer as a pepper powder, seasoning, or as a seasoning in foods or beverages.

Oleoresin

The plant product may take the form of an oleoresin or extract prepared from fruit pods harvested from a *Capsicum* plant, prepared by any means known in the art.

Press Cake

The plant product may take the form of press cake (press solids) produced as a by-product in the press extraction of oleoresin from fruit pods of *Capsicum* plants, prepared by, but not limited to, the method of U.S. Pat. No. 5,773,075. The press cake may be used for animal or human nutrition.

Refined Oleoresin

The plant product may take the form of an oleoresin or extract prepared from fruit pods harvested from a *Capsicum* plant, which has been further processed by any suitable techniques for processing botanical extracts known in the art, including, but not limited to centrifugation, decanting, precipitation (through seeding or through addition of other substances that facilitate precipitation), filtration, crystallization or recrystallization, saponification, chromatography, membrane processing or zone refining, to produce a material with a higher concentration of zeaxanthin than is present in the initially extracted oleoresin form. The zeaxanthin may be present in these materials in esterified or non-esterified form.

The oleoresin derived from a *Capsicum* plant of the instant invention may be refined by the process described by U.S. Pat. No. 6,504,067, the process of which is hereby incorporated by reference. The process includes: 1) refining the plant extract or oleoresin by treatment with a diluted aqueous alkaline solution which forms a first oleoresin phase and a first aqueous phase containing impurities, 2) treating the first oleoresin phase with diluted aqueous organic or inorganic acid, 3) forming a second oleoresin phase and a second aqueous phase containing impurities, and 4) separating the second aqueous phase containing impurities from the second oleoresin phase to obtain the refined carotenoids.

Isolated and Refined Zeaxanthin

Extracts of *Capsicum* plant pod flesh can be further processed to provide zeaxanthin in different forms and purities. Further processing methods include, but are not limited to, centrifugation, decanting, precipitation (through seeding or through addition of other substances that facilitate precipitation), filtration, crystallization or recrystallization, saponification, chromatography, membrane processing or zone refining. The zeaxanthin may be present in these materials in esterified or non-esterified form.

For example, U.S. Pat. No. 5,648,564 discloses a process for forming, isolating and purifying xanthophyll crystals, preferably lutein from marigold flower petals, zeaxanthin from wolfberries or capsanthin and capsorubin from red pepper. A xanthophyll diester-containing plant extract is saponified in a composition of propylene glycol and aqueous alkali to form xanthophyll crystals. Crystallization is achieved without the use of added organic solvents. The crystals are isolated and purified. The substantially pure xanthophyll crystals so obtained are suitable for human consumption and can be used as a nutritional supplement and as an additive in food.

The crystallization process can be used for the purification of xanthophylls from a saponified extract. U.S. Pat. No. 6,329,557 describes a process comprising the steps of dispersing the saponified extract in water to form a dispersion, mixing the dispersion under conditions such that a portion of any water-soluble compounds dissolves in the water to form an aqueous phase and a residue that is not soluble in water, separating the aqueous phase from the residue, contacting the residue with a non-polar solvent under conditions such that a portion of any lipid-soluble compounds dissolves in the non-polar solvent and a portion of the xanthophylls precipitates from the non-polar solvent to form a precipitate, separating the non-polar solvent from the precipitate, washing the precipitate with a polar solvent such that at least a portion of any remaining chlorophylls dissolves in the polar solvent, and separating the polar solvent from the precipitate to yield a product comprising the xanthophylls at a desired level of purity.

Purified Zeaxanthin in Non-Esterified Form

Zeaxanthin esters from *Capsicum* plants may be saponified by a number of methods described in the art, and they include, but are not limited to: 1) saponification in water with acid or base, 2) saponification in methanol or isopropyl alcohol with acid or base, 3) saponification in propylene glycol with acid or base, and 4) saponification using enzymes.

Oleoresin from the extraction of zeaxanthin from *Capsicum* plants may be saponified in order to generate free zeaxanthin. This free, all-trans 3R,3'R isomer of zeaxanthin can be crystallized to obtain a purified form. Thus, the free, all-trans 3R,3'R isomer of zeaxanthin may be formulated in ways similar to those used for all-trans beta-carotene. A specific method for producing crystals of lutein and zeaxanthin is described in U.S. Pat. No. 5,648,564.

There are advantages and disadvantages associated with xanthophylls in their esterified or free forms. U.S. Pat. No. 6,689,400 discloses that free lutein is especially vulnerable to chemical and biological deterioration with respect the esterified form. On the other hand, it is disclosed in U.S. Pat. No. 5,997,922 that the free form of xanthophylls is more readily absorbed by chickens for egg and flesh pigmentation. The diester form of lutein appears to be more bioavailable in humans than the non-esterified form (Bowen et al., 2002). Breithaupt et al., 2004 observed enhanced bioavailability of 3R,3'R zeaxanthin dipalmitate compared with the non-esterified form in humans.

Purified Zeaxanthin in Re-Esterified Form

Short chain organic acids may be reacted with free zeaxanthin to produce short chain organic acid mono- or diesters of zeaxanthin. These short chain organic acids may be obtained by reacting organic anhydrides with a zeaxanthin extract, as described in U.S. Pat. No. 5,959,138. The organic anhydrides that may be used include but are not limited to acetic anhydride, propionic anhydride, and combinations thereof. Other esters may be formed by esterification processes involving other carboxylic acids, their anhydrides or esters. Additional zeaxanthin esters can be produced using transesterification reactions wherein zeaxanthin esters are treated with carboxylic acids and an acid, base or enzyme catalyst.

In the case of modified ester forms of zeaxanthin, the carboxylic acid moieties can consist of short chains ($C_1$ to $C_4$), medium chains ($C_5$ to $C_{12}$), or longer chains ($C_{13}$-$C_{30}$). The carboxylic acid moieties can be saturated, unsaturated or polyunsaturated. The carboxylic acid moieties can have linear or branched structures.

Isomers of Zeaxanthin

The zeaxanthin present in *Capsicum* plants consist primarily of the 3R,3'R stereoisomer. The pigments found in the fresh fruit of *Capsicum* plants are overwhelmingly in the all-trans configuration. Trans zeaxanthin can be converted in whole or in part into various cis forms by methods known in the art (Khachik, et al., 1992; Updike et al., 2003).

Oleoresin or Purified Forms of Zeaxanthin Dispersed in Oils, Fats, Emulsifiers or Stabilizers, or Combinations Thereof.

Zeaxanthin derived from *Capsicum* plants can be formulated with human-edible or animal-edible ingredients to facilitate its use as nutritional or feed supplements, food or feed colorants, or food or feed additives. Paprika oleoresin or more highly refined forms of zeaxanthin can be standardized in regard to coloring power by the addition of vegetable oils, such as corn oil, soybean oil, canola oil, peanut oil, sunflower oil, safflower oil, olive oil, cottonseed oil, palm oil, coconut oil, medium chain triglycerides, triacetin, hydrogenated vegetable oils, animal fats, such as lard tallow and poultry fat, fish oil, whale oil, algal oil and the like. Paprika oleoresin or more highly refined forms of zeaxanthin can be combined with food grade additives, including emulsifiers, such as lecithin, hydroxylated lecithin, monoglycerides, diglycerides, sorbitan esters, such as Polysorbate-80, sucrose esters, polyglycerol esters, tartaric acid esters of mono and diglycerides, and the like. Specifically, zeaxanthin can be made into a homogeneous liquid condimental composition useful in flavoring or coloring foods and beverages and which is dispersible in both oil and water, comprising: (1) hydroxylated lecithin, (2) tartaric acid esters of mono and diglycerides, and (3) one or more condiments selected from edible flavorings, edible coloring agents, one of which must be zeaxanthin derived from the present invention, the ratio by weight of (1) plus (2) to (3) being at least 1:4. Paprika oleoresin or more highly refined forms of zeaxanthin formulated with food-grade emulsifiers are particularly useful in beverage applications and emulsion-based foods.

Paprika oleoresin or more highly refined forms of zeaxanthin may be combined with natural and synthetic antioxidants known in the art. These include, but are not limited to: extracts of *Labiatae* herbs (including rosemary, sage, oregano, peppermint, basil, spearmint, summer savory), olive extracts, coffee extracts, citrus extracts, tea extracts, tea catechins, catechin, epi-catechin, epi-catechin gallate, epi-gallocatechin gallate, gallic acid, tocopherols, tocotrienols, ascorbic acid and ascorbates (including ascorbyl palmatate), erythorbic acid and erythorbates, glutathione, carnosic acid, carnosol, rosmanol, rosmarinic acid, salviaflaside, flavonoids or flavonoid glucuronides (including quercitin, luteolin, apigenin, or glucuronides of quercitin luteolin, and apigenin and the like), curcumin, tetrahydrocurcumin, hydroxy tyrosol, oleuropein, BHT, BHA, hydroxylamines, propyl gallate, ethoxyquin, Trolox or TBHQ; or mixtures thereof. Stabilization of standard paprika oleoresins with tetrahydrocurcuminoids is described in U.S. Pat. No. 6,689,400.

Oleoresin or Purified Forms of Zeaxanthin in Combination with Other Carotenoids, Pigments, or Food Colors, or Combinations Thereof.

Paprika oleoresin or more highly refined forms of zeaxanthin can be combined with one or more other natural and/or synthetic carotenoids to provide mixed carotenoid compositions useful as nutritional or feed supplements, food or feed colorants, or food or feed additives. Examples of other natural and/or synthetic carotenoids that can be combined include, but are not limited to: carrot extract, synthetic beta carotene, tomato extract, synthetic lycopene, marigold extract, synthetic lutein, annatto extract, bixin, norbixin, beta-apo-8-carotenal, canthaxanthin, astaxanthin, lutein, algal carotenoids, fungal carotenoids, cryptoxanthin, alpha-zeacarotene, beta-zeacarotene, and the like.

Paprika oleoresin or more highly refined forms of zeaxanthin can be combined with other natural or synthetic approved food colorants to create compositions useful for providing a range of color hues for food or feed applications. Natural or synthetic colorants that can be combined include, but are not limited to: turmeric extract, purple carrot extract, anthocyanins, grape skin extract, beet extract, cabbage extracts, elderberry extracts, caramel, betalins, chlorophyll and approved FD&C food colorants.

Oleoresin or Purified Forms of Zeaxanthin Dispersed on Solids Suitable for Nutritional Supplement, Food, Beverage, Cosmetic or Pharmaceutical Applications.

Zeaxanthin in an oleoresin or more highly purified form may be dispersed onto a wide variety of solid carriers suitable for use in a wide variety of applications. The carriers can include salt, dextrose, maltodextrin, lactose, lignin, flour, talc, titanium dioxide, pharmaceutical and cosmetic excipients or other solid substrates or combinations thereof. Stable cold-water dispersible preparations of carotenoids produced from zeaxanthin obtained from *Capsicum* plants comprise carotenoids and a water-soluble or water-dispersible lignin derivative used in place of gelatin from warm-blooded animals (U.S. Pat. No. 5,668,183). The lignin derivatives for the preparations can contain a single lignin or a mixture of several lignin derivatives. Sodium, calcium, and ammonium lignosulphonate are especially preferred.

In addition, cold water dispersible forms can be made using starches, gums, or other methods known in the art.

Oleoresin or Purified Forms of Zeaxanthin in the Form of Beadlets Suitable for Nutritional Supplement, Food, Beverage, Cosmetic or Pharmaceutical Applications.

Beadlets, or microcapsules may be made that contain zeaxanthin, in any of its forms. Typical carotenoid concentrations range between 1 and 50 percent by weight. The microcapsules release the encapsulated carotenoids during the ingestion process. These microcapsules may also be suitable for use in human or animal foods, multivitamins, dietary supplements, and personal care products. They may also be used in tableting and capsules.

Zeaxanthin used to make beadlets may be either in the form of a crystalline powder or oil dispersion. Starting with a crystalline powder is preferable in some cases so that beadlets containing higher concentrations of zeaxanthin may be obtained.

Either chemical or physical methods of microencapsulation known in the art can be used to encapsulate zeaxanthin from the instant invention. Chemical methods of microencapsulation include, but are not limited to those involving: phase separation, solvent evaporation, solvent extraction, interfacial polymerization, simple and complex coacervation, in-situ polymerization, liposome technology, nanoencapsulation, sol-gel methods, vapor-phase deposition, entrapment/matrix encapsulation, macroemulsion, dispersion polymerization, desolvation, and gelation. Physical methods for encapsulation include but are not limited to spray drying, spray cooling, rotary disk atomization, fluid bed coating, stationary nozzle coextrusion, centrifugal head coextrusion, submerged nozzle coextrusion, pan coating, vibrating nozzle, extrusion, prilling, and annular jet methods.

In one form of the process, the crystalline powder is added to a fluidized bed dryer and the flow of heat and gas started. A liquid coating material is sprayed onto the solid to the desired formulation. The liquid coating material may comprise, but is not limited to an aqueous solution of a sugar, or sorbitol, a starch or maltodextrin, and optionally a coating protein such as gelatin. Details of the process are disclosed in U.S. Pat. No. 6,663,900. Zeaxanthin-rich oil dispersions or higher-purity crystalline forms of zeaxanthin can be encapsulated in a matrix such as that described in U.S. Pat. No. 5,786,017, U.S. Pat. No. 5,506,353 and U.S. Pat. No. 6,607,771.

Zeaxanthin derived from the instant invention may be combined with matrix materials known in the art in the process of encapsulation. In general, hydrocolloids, carbohydrates, and other compounds may be used. Hydrocolloids include, but are not limited to gelatin, milk proteins, vegetable proteins, animal proteins, gums, and modified starches. The carbohydrates include, but are not limited to sucrose, glucose, and dextrins. Other components include antioxidants, emulsifiers, stabilizers, and weighting agents.

Zeaxanthin derived from the instant invention may be combined with surface ingredients known in the art in the process of encapsulation. These agents include, but are not limited to proteins, carbohydrates, silicates, polysaccharides, polyhydric alcohol, waxes, fats, natural and synthetic polymers, resins, gelatin, polyvinyl alcohol, maltodextrin, methyl cellulose, polyvinyl pyrrolidone, and polyoxymethylene urea.

Zeaxanthin derived from the instant invention may be placed into microcapsules for improved heat, chemical, light, and oxidative stability; for better shelf life; and for improved color, odor, taste-masking, and handling. Zeaxanthin derived from the instant invention in encapsulated form may improve bioavailability; modify solubility; and offer controlled, sustained, delayed, pulsatile, pH induced, or targeted release.

Oleoresin or Purified Forms of Zeaxanthin in the Form of Emulsions.

Emulsions of zeaxanthin derived from *Capsicum* plants can be formed by techniques well known in the art. Emulsions of zeaxanthin may be prepared for use in aqueous systems of food, beverage, cosmetic, pharmaceutical and personal care products. The combination of a surfactant, zeaxanthin, optionally in an oil carrier, and, optionally, an anti-foaming agent are used to produce an aqueous emulsion. The emulsion may be dried to form a powder that is readily dispersible in an aqueous medium. The zeaxanthin used in emulsions can take the form of a crude oleoresin or a more highly purified form of zeaxanthin that is either free zeaxanthin or zeaxanthin in an esterified form.

Alternatively, an emulsion of zeaxanthin may be prepared following U.S. Pat. No. 6,296,877 as: 1) preparing a homogenous solution of zeaxanthin optionally with an emulsifier and optionally an edible oil in a water miscible organic solvent, 2) mixing this solution with an aqueous solution of a mixture of protective colloids, and optionally 3) preparing a water-dispersible dry powder by freeing the resulting dispersion from the solvent and water and drying it.

Oleoresin or Purified Forms of Zeaxanthin in the Form of Spray-Dried or Encapsulated powders suitable for nutritional supplement, food, beverage, Cosmetic, Personal Care or Pharmaceutical Applications.

Zeaxanthin derived from *Capsicum* plants is suitable for processing into powdered forms. Emulsions of zeaxanthin oleoresins or dispersions of zeaxanthin crystals or pulverized forms of zeaxanthin can be spray dried using technology known in the art. Commonly, an oil dispersion or solution of zeaxanthin is mixed with water and a polymeric material, such as gelatin, vegetable gum, modified starch, dextrin, or non-gelling proteins. An emulsifier is added and the mixture is homogenized. The resulting emulsion is atomized and introduced into a heated column of air in a drying chamber, and free-flowing powders are produced as the water is evaporated. An example of this kind of method is described in U.S. Pat. No. 6,635,293. Solid zeaxanthin forms can be encapsulated by any of a variety of techniques known in the art, including fluid bed agglomeration or coacervation.

Another example of producing a dry product is disclosed in U.S. Pat. No. 3,998,753. Carotenoid powder compositions derived from *Capsicum* plants that are dispersible in aqueous solutions and that form optically clear aqueous compositions that color these aqueous solutions to a desired uniform color can be made as follows. First, a solution of a carotenoid in a volatile organic solvent capable of solubilizing carotenoids is formed and emulsified with an aqueous solution containing a food-grade surfactant using high-speed mixing. The volatile solvent is then removed from the resulting emulsion by heating the emulsion while maintaining the high speed mixing with high shear until the solvent is completely removed. The emulsion can then be used as is or dried to yield carotenoid-containing powder compositions.

Oleoresin or Purified Forms of Zeaxanthin Encapsulated in a Manner to Allow Incorporation into Nutritional Supplement, Food, Beverage, Cosmetic or Pharmaceutical Applications, without Altering the Color of the Nutritional Supplement, Food, Beverage, Cosmetic or Pharmaceutical.

Zeaxanthin particles or particles containing zeaxanthin can be coated with opaque materials that effectively hide the color of the pigment. This is a useful technique if it is desired to add zeaxanthin to a product without changing the product's color.

Applications of Zeaxanthin Formulations

Zeaxanthin-Rich Food

Fruit pods from the *Capsicum* varieties of the present invention exhibiting a hyper-accumulation of carotenoid pigment may be used directly as a human food and the juice expressed from them used as a drink. The *Capsicum* fruit pods may be consumed in the fresh or dried state. These forms may be ground, chopped, or liquefied for use alone or in combination with any other food, sauce, or beverage. The material may be used as a component in a seasoning or condiment.

Food Color Applications

Naturally derived carotenoids have attained considerable importance as coloring agents, and their importance has increased due to government regulations withdrawing or limiting the use of certain previously certified coloring agents. The pigment in the *Capsicum* varieties of the present invention is acceptable as a food coloring agent in the United States under FDA regulation (21 CFR §73.340). *Capsicum*-derived pigment is the only known source of zeaxanthin that can be used as a food colorant under current food regulations. There is considerable interest in the availability of light-stable yellow colorants in the food industry to replace the light-unstable curcumin pigments derived from turmeric (*Curcuma longa*). Zeaxanthin products derived from the *Capsicum* varieties can be added to various foods and beverages for human consumption as a nutritional food-coloring agent to provide a bright, natural yellow appearance with high light stability relative to turmeric.

Fat containing foods including, but not limited to, butter, margarines, vegetable oils, chocolate, baked goods such as cakes, breads, bagels, crackers, pizza dough, pancakes and waffles and mixes for these, fillings, peanut butter, salad dressings, processed cheese, processed meats, seasoning blends and sauces can all be colored by the addition of the inventive zeaxanthin oleoresins or purified forms of the inventive compositions dispersed in oils, fats and emulsifiers. Said formulations of the instant *Capsicum* varieties containing high concentrations of zeaxanthin may also contain natural and synthetic antioxidants known in the art.

Dry food products including, but not limited to, bakery mixes including bread mix, bagel mix, cake mix, pizza dough mix, cereals, dry soups, seasoning blends, tomato powder, cereals, macaroni, pasta flour, nutritional and energy bars can all be colored by direct addition of powdered formulations of zeaxanthin. These powder formulations may have been produced by spray-drying, encapsulation or dry dispersing the oleoresin or refined oleoresin onto a dry carrier. Said formulations may also contain natural and synthetic antioxidants known in the art.

Seasoning formulations comprising the inventive zeaxanthin compositions in combinations with flavoring and/or preserving agents are contemplated. Flavoring agents include but are not limited to spice and herb extractives, synthetic flavorings, essential oils, fixed oils, and the like. Preserving agents include but are not limited to natural and synthetic antioxidants known in the art, some of which are listed above. These compositions can optionally include carriers and/or excipients including but not limited to vegetable oils, ethanol, water, propylene glycol, glycerin, benzyl alcohol, monoglycerides, diglycerides, and other emulsifiers or combinations thereof as described above or known in the art.

Coloring formulations comprising the inventive zeaxanthin compositions in combinations with coloring and/or preserving agents are contemplated. Coloring agents include but are not limited to extracts of *Bixa orellana, Curcuma longa, Daucus carota sativa, Capsicum annuum* (other than the instant plant), *Dunaliella saline, Haematacoccus pluvalus*, beta-carotene, beta-apo-8-carotenal, the ethyl ester of the beta-apo-8-carotenoic acid, synthetic colors (FD&C coloring agents), and the like. Preserving agents include but are not limited to natural and synthetic antioxidants known in the art, some of which are listed above. These compositions can optionally include carriers and/or excipients including but not limited to vegetable oils, ethanol, water, propylene glycol, glycerin, benzyl alcohol, monoglycerides, diglycerides, and other emulsifiers or combinations thereof as described above or known in the art.

Aqueous-based foods including, but not limited to, sauces, including tomato sauce, steak sauce, and pizza sauce, gravies, soups, gelatins, puddings, eggnog, ketchup, pickles, salad dressings, egg yolks, meat marinades, dairy products, such as milk, yogurt, and ice cream, can all be colored by direct addition of water soluble powdered formulations of zeaxanthin. They may alternately be colored by the addition of zeaxanthin oleoresin, which has been admixed with emulsifiers such as mono-glycerides, tartaric acid esters of triglycerides, lecithins, polysorbates sucrose fatty acid esters or hydroxylated lecithins, or mixtures thereof, to form a water dispersible resin. Said formulations may also contain natural and synthetic antioxidants known in the art.

Beverages, including but not limited to, nutritional drinks, sodas, milk, beer, alcoholic beverages, fruit juices (including, but not limited to orange juice, apple juice, grape juice, cranberry juice, tomato juice, guava juice, mango juice, cantaloupe juice, carrot juice, and grapefruit juice), dairy beverages, soy beverages, infant formulas, adult formulas (including Ensure®—a registered trademark of Abbott Laboratories Corporation) and their concentrates can be colored or fortified with a zeaxanthin product in the form of water dispersible powders produced by spray drying or encapsulation. They may alternately be colored with aqueous emulsion or emulsified resin forms containing the zeaxanthin product. Said formulation may also contain natural and synthetic antioxidants known in the art.

There is a substantial body of published articles and patents relating to the formulation and use of beta-carotene and other carotenoids as food colorings, nutritional additives, feed supplement, cosmetic additives, personal care additives and pharmaceutical additives. Such publications include, for example, U.S. Pat. No. 4,522,743, U.S. Pat. No. 5,180,747, U.S. Pat. No. 5,350,773 and U.S. Pat. No. 5,356,636. Due to the similarities in the chemical and physical properties of zeaxanthin and beta carotene, or other carotenoids, any technique, additive, stabilizer, or other method for adding beta-carotene or other carotenoids to any type of food, cosmetic, feed, pharmaceutical, personal care or nutritional use is also likely to be directly applicable to the zeaxanthin compositions derived from the instant *Capsicum* varieties.

Cosmetics

Zeaxanthin derived from the instant *Capsicum* plants may be used in various types of cosmetic applications. It can be applied topically or taken internally for sun protection and as an antioxidant. Zeaxanthin can be used in lip applications such as lip balms, lipsticks, lip liners, lip moisturizers, and the like. Zeaxanthin may be used in cosmetic applications that include foundations, makeup, blushes, tanning creams, and the like. It can also be used in topical products that are applied to the skin for protection from the effects of radiation, such as that from the sun. These products include tanning lotions, tanning accelerators, tanning moisturizers, and the like. An example of using zeaxanthin in cosmetic applications is U.S. Pat. No. 6,110,478, which discloses a composition for cosmetic purposes which is a regulator of cutaneous pigmentation and is adapted both to administration by the oral route and to application on the skin.

Animal Feed

Zeaxanthin derived from the instant *Capsicum* varieties may be administered to animals in order to pigment their flesh, skin or their eggs, or to serve as a nutritional supplement.

Pigmentation of Fish and Crustaceans

Zeaxanthin derived from the instant *Capsicum* varieties may be administered to fish or crustaceans in order to pigment their flesh. For example, salmon can be fed the inventive product in order to create a flesh tone that is appealing to consumers. Likewise the flesh of crustaceans such as shrimp, prawns, lobsters, and crawfish can be pigmented to a more desirable product color.

Broiler Skin and Egg Pigmentation

The color of poultry broiler skin and of egg yolk is widely known as an important quality attribute. Each region of the world has established its own particular specification for this parameter. Thus, the optimum pigmentation of broiler skin and egg yolk depends on cultural traditions and preferences. Traditionally, poultry keepers have been incorporating red and yellow pigments (natural or synthetic) into the bird's feed.

Synthetic canthaxanthin has been used for decades as a pigment to provide a yellow-orange color to poultry broiler skin, and to provide intense orange and even rose hues to egg yolk (U.S. Pat. No. 5,997,922).

U.S. Pat. No. 3,539,686 discloses that it is possible to obtain a wide range of tones going from yellow to red hues in broiler skin and egg yolk, by using blends of xanthophylls or zeaxanthin with one or more pigments such as canthaxanthin, beta-apo-8-carotenal, ethyl ester of the beta-apo-8-carotenoic acid, and extracts from paprika and red peppers. U.S. Pat. No. 3,539,686 discloses that it is a requirement to use a red pigment in order to obtain more intense orange or reddish hues, as compared with the hues obtained if only yellow xanthophylls were used, because of the synergistic effect obtained when both pigments are used.

A great amount of research has been performed to determine the different proportions of yellow xanthophylls and red pigments in order to obtain specific hues in broiler skin and in egg yolk (see U.S. Pat. No. 5,997,922). It has been demonstrated that zeaxanthin provides more efficient pigmentation than lutein, by imparting an orange hue to the broiler skin.

Traditional sources of yellow xanthophylls are alfalfa, yellow corn gluten, and marigold meal concentrates, wherein it has been demonstrated that the saponified natural pigment has a better bioavailability than the non-saponified pigment in poultry (U.S. Pat. No. 5,997,922).

A preparation of a saponified marigold extraction with a high content of zeaxanthin, called Hi-Gold® (Organica, S.A. de C.V.) obtained by a process for the isomerization of lutein contained in the extract, as is described in U.S. Pat. No. 5,523,494. This patent describes the application of Hi-Gold® for broiler skin and egg yolk pigmentation purposes eliminating the use of red pigments. Furthermore, it has been demonstrated that by using Hi-Gold®, deeper hues are obtained in broiler skin and egg yolk than those obtained when only the traditionally yellow pigments are used alone.

U.S. Pat. No. 5,997,922 discloses a method for orange tone pigmentation of broiler skin and egg yolk, comprising: dosing about 8 to 55 ppm of saponified xanthophylls having a zeaxanthin content of about 20 to 80% in the feed, beverage, or broth, of broilers and laying hens, in the absence of natural or synthetic red pigments.

Zeaxanthin derived from the instant *Capsicum* varieties may be used for pigmentation of broiler skin and egg yolk.

Animal Nutrition

Zeaxanthin derived from the instant *Capsicum* varieties may be administered to pets, livestock, and other animals as a dietary supplement as well as to prevent diseases such as cataracts, AMD and other degenerative diseases. The inventive zeaxanthin may be used as a dietary supplement for dogs, cats, cattle, horses, sheep, fish, goats, rabbits, chickens, turkeys, and other animals. Zeaxanthin may be administered to these animals in a wide variety of forms known in the art. This includes, but is not limited to tablets, dips, food, treats, and pellets. In aquaculture, zeaxanthin may be used to impart a desired color to the body and/or flesh.

Human Nutrition

Zeaxanthin is disclosed to be effective in the treatment of a variety of eye diseases (U.S. Pat. No. 5,854,015). Stereoisomeric forms of zeaxanthin and their use in the treatment and prevention of AMD and other eye disorders is disclosed in U.S. Pat. No. 6,329,432. Zeaxanthin derived from the instant Capsicum varieties confers advantages over the zeaxanthin compositions of the prior art for the reasons identified herein and are summarized again as follows:

1. The zeaxanthin compositions derived from the instant Capsicum varieties do not contain nor were ever contacted with phototoxic or contact dermatitis sensitizing agents.
2. The zeaxanthin compositions derived from the instant Capsicum varieties can be used as a natural food colorant under existing food regulations.
3. The zeaxanthin compositions derived from the instant Capsicum varieties are GRAS and can be used as a food additive.
4. The zeaxanthin compositions derived from the instant Capsicum varieties are natural products.
5. Fruits of Capsicum are a common food source.

All patents cited in this application are herein incorporated by reference.

EXPERIMENTAL PART

The subject matter of the instant invention will be better understood in connection with the following examples, which are intended as an illustration of and not a limitation upon the scope of the invention. It will be apparent to those skilled in the art that the described examples are merely representative in nature.

Example 1

Development of a Capsicum Plant Exhibiting High Concentrations of Zeaxanthin

The instant Capsicum plants exhibiting high concentrations of zeaxanthin in the ripe fruit pod flesh were developed using classical plant breeding methods, and methods known to those skilled in the art, which are understood in the art to encompass inbreeding and out-crossing, using a commercial Capsicum annuum variety NM plant type as a source of plant breeding material. The instant varieties resulted from the development of plant varieties which exhibit a high concentration of carotenoid pigments in the fruit pods. High carotenoid concentration and appropriate plant habit are desired for commercially adapted varieties.

During breeding and selection, Capsicum plants of the instant invention, exhibiting high concentrations of zeaxanthin in the ripe fruit pod flesh, may easily be distinguished from the wild type red-fruited variety by its distinguishing orange color. Capsicum plants of the instant invention exhibit a sufficiently different appearance to allow one skilled in the art to distinguish it from other Capsicum annuum varieties.

Screening for Capsicum varieties exhibiting high concentrations of zeaxanthin in the ripe fruit pod flesh, is routinely carried out by first selecting for the desired plant morphology and subsequent analysis of carotenoid composition in the fruit. Capsicum plants exhibiting high zeaxanthin concentrations in the mature fruits can predictably be bred by inbreeding the commercially grown NM variety, NM 1441, deposited at the American Type Culture Collection (ATCC) under the deposit designation PTA-10729, as a parental strain (NM 1441×NM 1441). As the plant habit and color of ripe fruit pods of the instant Capsicum variety exhibit a phenotype which is markedly different from the parental variety, screening for plants exhibiting the desired phenotype is easily carried out by visual inspection of the plant rows. Obtaining a Capsicum plant with the desired zeaxanthin composition by using the breeding methods described herein is a relatively rare, but a repeatable event. For example, 5 Capsicum plants exhibiting high concentrations of zeaxanthin in the ripe fruit pod flesh were obtained after evaluation of about 102,000 plants in a test plot. Routine screening of this number of plants for the desired phenotype was easily carried out by row evaluation for the readily identifiable visual differences in the mature fruit of the instant variety (orange fruit) compared to the parental, or wild-type variety (red fruit) and the morphological differences in plant habit. Following selection, the zeaxanthin content in the ripe fruit pod flesh was confirmed by HPLC analysis.

Using similar methods, other plants of the Capsicum genus can be used to develop varieties that hyper-accumulate zeaxanthin.

Example 2

Describing Small-Scale Field Production

A small test plot of the Capsicum varieties of the instant invention was planted. After 6 months, the crop was treated with a defoliant and allowed to dry in the field. The crop was hand-harvested. The fruit pods were sliced and dehydrated in a commercial continuous gas-fired oven. Two composite samples of the dried fruit pods from production were analyzed as described in Examples 6, 8 and 9. The mass percent zeaxanthin relative to total carotenoids was 70.81% and 71.80%. The weight percent of zeaxanthin in the ripe, dried fruit pods was 0.93% and 0.97%.

Example 3

Describing Field Production

A test plot of the instant Capsicum varieties was planted. After 6 months, the crop was treated with a defoliant and allowed to dry in the field. The crop was hand-harvested. The fruit pods were sliced and dehydrated in a commercial continuous gas-fired oven. Seven lots of fruit pods were harvested and representative samples of each were analyzed as described in Examples 6, 8 and 9. The mass percent zeaxanthin relative to total carotenoids in the seven samples was 57.7%, 59.7%, 61.3%, 59.1%, 59.6%, 53.3%, and 60.9%. The mass percent of zeaxanthin in the dried, ripe fruit pods was 0.76%, 0.81%, 1.0%, 0.96%, 0.70%, 0.83%, and 0.87% of the total dried ripe fruit pod flesh, respectively.

Example 4

Extraction of the Instant Capsicum Varieties on a Commercial Scale 2894 pounds of the dried, ripe fruit pods of the instant Capsicum plants from Example 2 was ground and solvent-extracted with mixture of hexane and acetone (65:35) in a continuous basket extractor. The miscella was desolventized to less than 25 ppm hexanes and acetone using a vacuum stripper to obtain 194 pounds of a Capsicum oleoresin. The oleoresin contained 6.7% total zeaxanthin, measured as free zeaxanthin after a saponification step (using the methods of Examples 7 and 9).

Example 5

Determination of Zeaxanthin Stereochemistry

The optical isomer present in the oleoresin was determined by analysis in a commercial laboratory. Ground input material was extracted as in Example 4 and saponified on a small scale, along the lines of Example 6. This saponified sample was dissolved in tetrahydrofuran and diluted for carotenoid analysis on a C30 column using gradient separation. For optical isomer analysis, the samples were dissolved in hexane and examined by normal-phase HPLC for xanthophyll content. For samples containing multiple peaks, the zeaxanthin peak was collected from multiple injections on this system. The combined collection was re-injected to ensure that only trans-zeaxanthin had been collected. The combined collections were concentrated under nitrogen and injected onto a series of two chiral Chiralcel® OD columns (4.6×250 mm, 5 µm) (Daicel Chemical Industries, LTD, Fort Lee, N.J.). The mobile phase used in the separation was 5% isopropanol in hexane at a flow rate of 0.6 mL/min. The analytes were detected at 450 nm. A neat standard of 3R,3'R zeaxanthin was injected with each set of samples to verify the retention time. For any samples in which the retention time of the zeaxanthin peak did not match that of 3R, 3'R zeaxanthin, the samples were spiked with this standard and re-injected to distinguish between retention time shifts and distinctly different peaks. The sample was found to contain only one optical isomer that was identified as 3R, 3'R zeaxanthin.

Example 6

Saponification Procedure of Ground *Capsicum* for HPLC Analysis

Ground, ripe, dried fruit pod flesh of the instant *Capsicum* varieties (1.0 g) was weighed to the nearest tenth of a milligram on an analytical balance and was quantitatively transferred to a 125 ml Erlenmeyer flask. The flask was immediately covered with aluminum foil to reduce exposure to light. Butylated hydroxytoluene (0.2 g, Sigma Chemical Company), and 1.5 g of sodium carbonate powder (Aldrich Chemical—A.C.S. reagent) were weighed and added to the Erlenmeyer flask. 50 ml of methanol (Fisher Scientific—HPLC-grade) and about 0.8 g of potassium hydroxide (VWR Intl.) were added to the Erlenmeyer flask. A stir bar was added to the solution and a Vigreux distilling column was attached to the top of the Erlenmeyer flask. The solution was placed on a hot plate and refluxed on low heat (~65° C.) with stirring for 1 hr. Then the solution was taken off the hot plate and allowed to cool. A total of 1.2 ml of phosphoric acid (Innophos 75% FCC grade; Innophos, Inc., Cranbury, N.J.) was added to neutralize the solution. The solution was vacuum filtered through a Buchner funnel containing Celite® (Eagle Picher Filtration and Minerals, Reno, Nev.) directly into a 200 ml volumetric flask. All the color was rinsed out of the Erlenmeyer flask and the Buchner funnel with methanol, combined and brought to a 200 ml total volume with methanol. After inverting the flask several times, the solution was poured into a 3 cc syringe with a 0.45 micron PTFE Acrodisc® (Gelman) filter and injected into an amber vial for HPLC analysis.

Example 7

Oleoresin Saponification Procedure for HPLC Analysis

Oleoresin derived from the instant *Capsicum* varieties (0.03 g) was weighed to the nearest tenth of a milligram on an analytical balance directly into a 125 ml Erlenmeyer flask. The flask was immediately covered with aluminum foil to reduce exposure to light. A total of 0.2 g of butylated hydroxytoluene (Sigma Chemical Company) and 1.5 g of sodium carbonate powder (Aldrich Chemical—A.C.S. reagent) were weighed and added to the Erlenmeyer flask. 50 ml of methanol (Fisher Scientific—HPLC-grade) and about 0.8 g of potassium hydroxide (VWR Intl.) were added to the Erlenmeyer flask. A stir bar was added to the solution and a Vigreux distilling column was attached to the top of the Erlenmeyer flask. The solution was placed on a hot plate and refluxed on low heat (~65° C.) with stirring for 1 hr. Then the solution was taken off the hot plate and allowed to cool. A total of 1.2 ml of phosphoric acid (Innophos 75% FCC grade) was added to neutralize the solution. The solution was vacuum filtered through a Buchner funnel containing Celite® (Eagle Picher Filtration and Minerals, Reno, Nev.) directly into a 200 ml volumetric flask. All the color was rinsed out of the Erlenmeyer flask and the Buchner funnel with methanol, combined and brought to a 200 ml total volume with methanol. After inverting the flask several times, the solution was poured into a 3 cc syringe with an 0.45 micron PTFE Acrodisc® (Gelman) filter and injected into an amber vial for HPLC analysis.

Example 8

Figure 2:
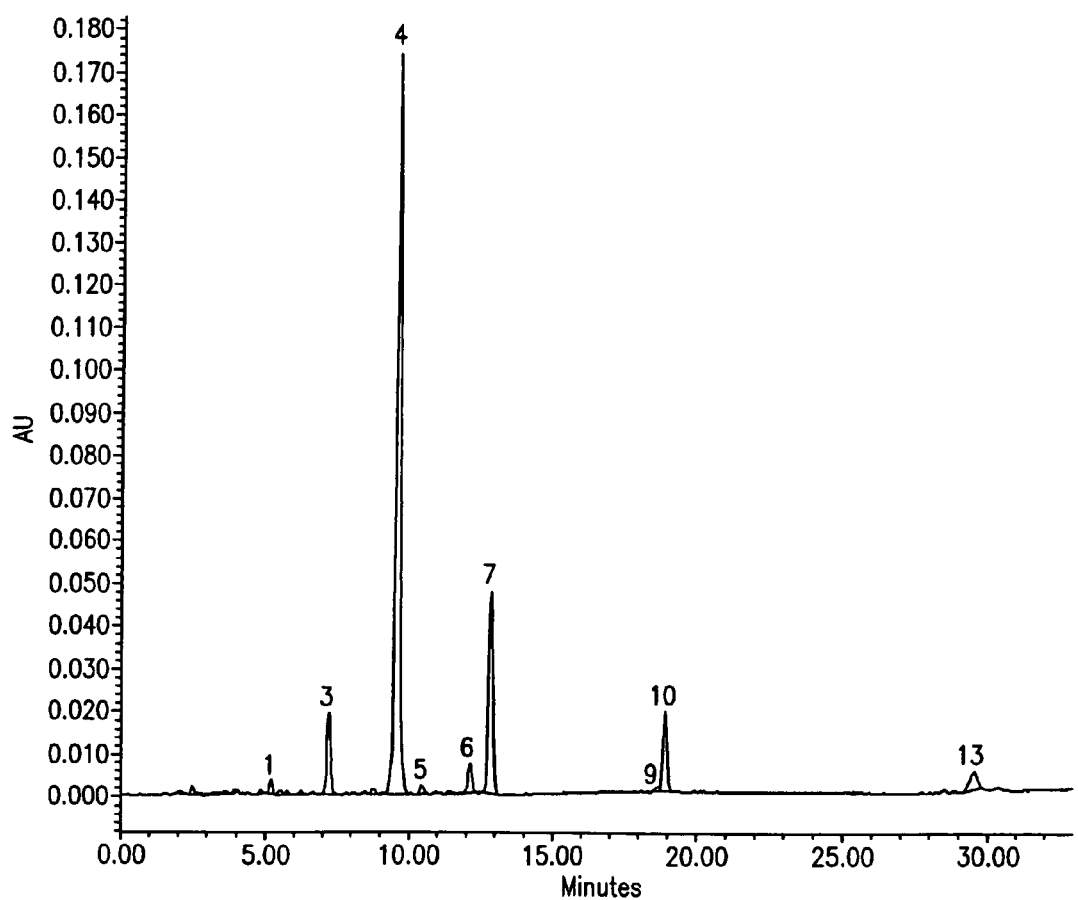
FIG. 2 is an HPLC chromatogram (maxplot 400 nm-600 nm) as set forth in Example 8, of saponified, ground, dried, ripe fruit pod flesh from *Capsicum* plants of the present invention. Peak identification is as follows: 1=capsorubin, 3=capsanthin, 4=trans-zeaxanthin, 5=lutein, 6=antheraxanthin, 7=9-cis-zeaxanthin, 9=α-cryptoxanthin, 10=β-cryptoxanthin and 13=trans-β-carotene. Ratios of zeaxanthin to total carotenoids were calculated by summing the area counts for all the zeaxanthin isomers and dividing that number by the total area count of all the carotenoid peaks.

Determination of the Percentage of Zeaxanthin Relative to Total Carotenoids (Area %) by HPLC Analyses were performed on a Waters 2695 (Milford, Mass. USA) separation system using Empower (Build 1154, Database version 5.00.00.00) software installed on the data station. The chromatographic separation was performed on a reverse-phase column (Waters Symmetry® C18, particle size 5 µm, 250 mm×4.6 mm). The eluent was a ternary gradient of methanol/water/acetone at 1.0 ml/min. The initial composition of the eluent was methanol-water-acetone (0:25:75, v/v/v). An initial linear gradient was applied for 15 minutes that yielded a composition of methanol-water-acetone (20:5:75, v/v/v). This composition was held for 15 minutes, followed by another linear gradient for 30 minutes to yield a composition of methanol-water-acetone (25:0:75, v/v/v). Finally another linear gradient was applied for 15 minutes yielding a composition of methanol-water-acetone (0:0:100, v/v/v). This composition was held for 5 minutes and returned to initial conditions. Compounds were detected (maxplot between 400 nm-600 nm) on a Waters 996 photodiode array detector using an injection volume of 20.0 µl. Literature retention times and PDA spectra were used to identify some of the peaks (viloxanthin, antheraxanthin, 9-cis-zeaxanthin, cryptocapsin, α-cryptoxanthin, ζ-carotene). Other compounds were identified and compared with standards from Carotenature (Lupsingen, Switzerland) and are listed as follows: capsorubin, capsanthin, trans-zeaxanthin, lutein, β-cryptoxanthin, α-carotene, trans-β-carotene and cis-β-carotene. Example chromatograms of saponified ground, ripe, dried fruit pods and saponified oleoresin from the instant *Capsicum* varieties are included as FIGS. 1 and 2, respectively.

Example 9

Determination of Zeaxanthin Content (Wt %) by HPLC

The analyses were performed on a Waters 2695 (Milford, Mass. USA) separation system using Empower (Build 1154, Database version 5.00.00.00) software installed on the data station. The chromatographic separation was performed on a reverse-phase column (Waters Symmetry® C18, particle size 5 μm, 250 mm×4.6 mm). The eluent was a ternary gradient of methanol/water/acetone at 1.0 ml/min. The initial composition of the eluent was methanol-water-acetone (0:25:75, v/v/v). An initial linear gradient was applied for 15 minutes and yielded a composition of methanol-water-acetone (20:5:75, v/v/v). This composition was held for 15 minutes, followed by another linear gradient for 30 minutes to yield a composition of methanol-water-acetone (25:0:75, v/v/v). Finally another linear gradient was applied for 15 minutes yielding a composition of methanol-water-acetone (0:0:100, v/v/v). This composition was held for 5 minutes and then returned to initial conditions. Compounds were detected (maxplot between 400 nm-600 nm) on a Waters 996 photodiode array detector using an injection volume of 20.0 μl. Zeaxanthin content was measured in reference to a calibration curve generated from a purchased authentic sample. Trans-zeaxanthin obtained from Carotenature (Lupsingen, Switzerland) was dissolved in methanol. This stock solution was used to generate a 5-point external calibration curve covering concentrations ranging from 2.0 μg/ml-45.0 μg/ml. 9-cis-zeaxanthin was quantified using the trans-zeaxanthin calibration curve, assuming a response factor of 1:1. Zeaxanthin contents are reported as a sum of all zeaxanthin isomers.

Example 10

Random Sampling of Production Field

Ten field samples of random individual *Capsicum* plants of the instant invention were harvested. The pods were de-seeded and dehydrated in a laboratory dehydrator and were subjected to analysis as described in Examples 6 and 8. The percentage of zeaxanthin relative to total carotenoids, measured in non-esterified forms, in each sample is shown below.

| Sample | % Zeaxanthin to total Carotenoids |
|---|---|
| 6203017a | 68.99 |
| 6203023a | 69.84 |
| 6203037a | 71.00 |
| 6203038a | 70.21 |
| 6203045a | 77.87 |
| 6203053a | 65.72 |
| 6203058a | 67.83 |
| 6203060a | 67.30 |
| 6203065b | 69.59 |
| 6203073a | 62.96 |

Example 11

Random Sampling of Production Field

Sixty-three field samples of random individual *Capsicum* plants of the present invention were harvested. The pods were de-seeded and dehydrated in a laboratory dehydrator and were subjected to analysis as described in Examples 6, 8 and 9. The percentage of zeaxanthin relative to total carotenoids, measured in non-esterified forms, in each sample is shown below. The mass percent of zeaxanthin, measured as the free diol, for selected samples is also shown. The HPLC method utilized the calibration curve described in Examples 8, and 9. The ASTA value and % zeaxanthin based on ASTA was determined by the method in Example 23.

| Sample | % Zeaxanthin to total Carotenoids | ASTA Value | Calculated mass % Zeaxanthin based on ASTA Value | Measured mass % zeaxanthin by HPLC |
|---|---|---|---|---|
| 9004008a | 73.2 | 539 | 1.0 | |
| 9004013a | 68.9 | 465 | 0.8 | |
| 9004027a | 70.7 | 490 | 0.9 | |
| 9004061a | 67.5 | 414 | 0.7 | |
| 9004075a | 76.3 | 454 | 0.9 | |
| 9004082a | 68.9 | 383 | 0.7 | |
| 9004085a | 75.2 | 548 | 1.1 | |
| 9004127a | 76 | 381 | 0.8 | |
| 9004183a | 73.1 | 426 | 0.8 | |
| 9004213a | 68.8 | 511 | 0.9 | |
| 9004214a | 75.9 | 494 | 1.0 | |
| 9004219a | 74 | 474 | 0.9 | |
| 9004289a | 73.4 | 517 | 1.0 | |
| 9004053a | 71.5 | 428 | 0.8 | |
| 9004098a | 73.7 | 422 | 0.8 | |
| 9004139a | 72.6 | 395 | 0.7 | |
| 9004189a | 74.5 | 349 | 0.7 | |
| 9004261a | 73.7 | 456 | 0.9 | |
| 9004299a | 65.9 | 430 | 0.7 | 0.885 |
| 9004343a | 74.1 | 344 | 0.7 | 0.761 |
| 9004395a | 73.6 | 423 | 0.8 | |
| 9004435a | 73.6 | 343 | 0.7 | |
| 9004492a | 61.8 | 448 | 0.7 | |
| 0090005a | 72.6 | 584 | 1.1 | 1.373 |
| 0115001a | 71.6 | 520 | 1.0 | |
| 0185002a | 70.8 | 523 | 1.0 | |
| 0199001a | 68.5 | 514 | 0.9 | |
| 0199002a | 65.1 | 561 | 1.0 | |
| 0220003a | 67.7 | 489 | 0.9 | 1.075 |
| 0320001a | 66.1 | 506 | 0.9 | |
| 0335002a | 70.7 | 524 | 1.0 | |
| 0360001a | 68.5 | 515 | 0.9 | |
| 0435004a | 65.5 | 510 | 0.9 | 0.989 |
| 8004003a | 69.5 | 546 | 1.0 | |
| 9004016a | 54.7 | 392 | 0.6 | |
| 9004029a | 69.8 | 543 | 1.0 | |
| 9004058a | 60.2 | 398 | 0.6 | |
| 9004068a | 67.2 | 481 | 0.8 | |
| 9004077a | 71.6 | 415 | 0.8 | |
| 9004087a | 69.6 | 318 | 0.6 | |
| 9004109a | 69.7 | 536 | 1.0 | |
| 9004120a | 71.2 | 506 | 0.9 | |
| 9004142a | 72.6 | 547 | 1.0 | |
| 9004155a | 75.4 | 435 | 0.9 | |
| 9004193a | 70.1 | 371 | 0.7 | |
| 9004211a | 72.6 | 557 | 1.1 | |
| 9004226a | 72.1 | 402 | 0.8 | |
| 9004234a | 72.8 | 548 | 1.0 | |
| 9004239a | 63.4 | 409 | 0.7 | |
| 9004311a | 68.1 | 506 | 0.9 | |
| 9004319a | 72.8 | 461 | 0.9 | |
| 9004328a | 68.8 | 478 | 0.9 | |
| 9004346a | 70.7 | 490 | 0.9 | |
| 9004348a | 71.5 | 508 | 0.9 | |
| 9004354a | 75.7 | 472 | 0.9 | |
| 9004362a | 56.6 | 388 | 0.6 | |
| 9004367a | 59.5 | 443 | 0.7 | |
| 9004374a | 50.9 | 523 | 0.7 | |
| 9004376a | 71.5 | 497 | 0.9 | |
| 9004396a | 72.8 | 516 | 1.0 | |
| 9004411a | 69.6 | 385 | 0.7 | |
| 9004432a | 57.3 | 490 | 0.7 | |
| 9004443a | 63.6 | 341 | 0.6 | |

Example 12

Determining α-terthiophene (α-terthienyl) Levels in Extracts of *Capsicum* Varieties of the Instant Invention and Commercial Sources of Zeaxanthin and Lutein by GC-EI-MS and GC-PFPD The analyses were performed on a Varian 3800 gas chromatograph in-line with a Saturn 2000 ion trap mass spectrometer. The mass spectrometer was operated in the electron ionization mode with scanning from 40 u to 650 u. The NIST Standard Reference Database, version 1.6 was used for peak identification. The GC-pulsed flame photometric detector was configured for sulfur-specific detection as per vendor specification. Data acquisition utilized the Varian Saturn GC/MS data station (v5.51). Gas chromatography was performed on a Supelco MDN-5S fused silica capillary column, 30 m×0.25 mm i.d., 0.25 um film (p/n 24384)). The column flow rate was 1.5 ml helium/minute; the injector temperature was 240° C.; the detector temperature was 230° C.; the oven temperature program was 120° C. to 260° C. at 8° C./minute, hold at 260° C. for 4.5 minutes; the injector split ratio was 1 for PFPD analysis and 20 for the GC-EI-MS runs. The injection volume was 0.5 μL.

Figure 3:
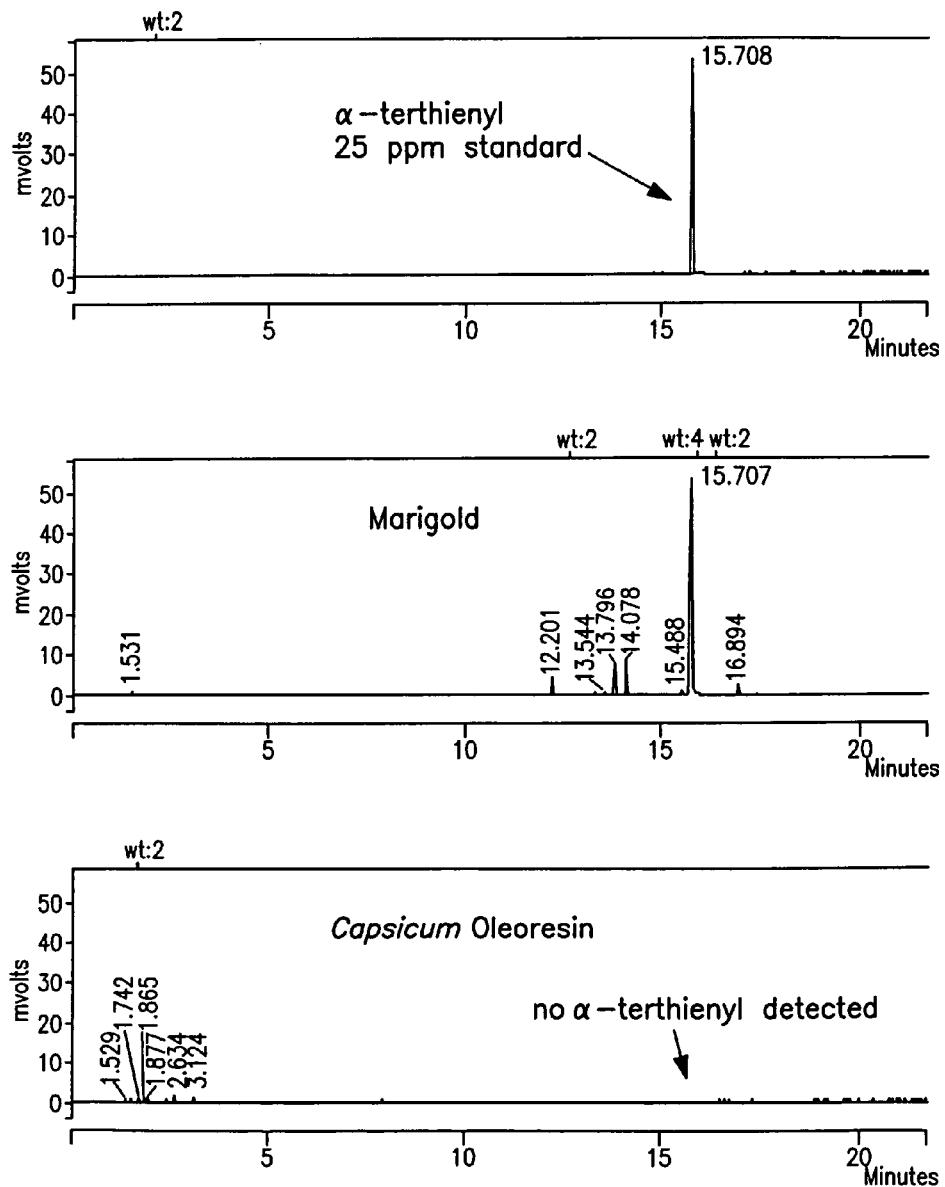
FIG. 3 shows chromatographic profiles for determining levels of α-terthienyl as in Example 12. The level of α-terthienyl in a commercial sample of Marigold oleoresin is compared to the α-terthienyl level in the *Capsicum* oleoresin of the present invention.

A PFPD calibration curve for α-terthienyl (Aldrich, 2,2': 5',2"-Terthiophene, #311073, 99% purity) from 160 ng per ml to 5000 ng per ml acetone was generated and used for subsequent quantitation. Oleoresin derived from the instant *Capsicum* plants, several commercial marigold oleoresins and two nutritional supplement capsules were tested. The respective oleoresins were dissolved in acetone at 3300 microgram of oleoresin per ml acetone prior to injection. The resulting sample area response was converted to the corresponding α-terthienyl ppm value from the calibration curve by solving the second order polynomial equation that was generated by a curve-fitting algorithm using Microsoft Excel 2000. The results are listed below. FIG. 3 shows a chromatographic comparison between the instant paprika oleoresin and a commercial marigold oleoresin.

| Sample | α-terthienyl concentration |
|---|---|
| Inventive Paprika Oleoresin | Non-detect |
| Commercial Zeaxanthin Capsule 1 | 1.4 microgram/capsule |
| Commercial Lutein Capsule 2 | 2.2 microgram/capsule |
| Commercial Marigold Extract 1 | 515 ppm |
| Commercial Marigold Extract 2 | 1150 ppm |
| Commercial Marigold Extract 3 | 760 ppm |

Lower limit of detection (LOD) is 1.0 microgram/capsule for capsules

Example 13

Saponification of Oleoresin Derived from the Instant *Capsicum* Varieties and Preparation of Compositions with Higher Zeaxanthin Levels Oleoresin from Example 4 (15.0 g), methanol (15 mL) and 45% aqueous potassium hydroxide solution (6 mL) was combined in a 125 mL Erlenmeyer flask, equipped with Vigreux distilling column and magnetic stir bar and the flask was wrapped in aluminum foil. The mixture was heated to reflux with stirring for 1.5 hours. The dispersion was transferred to a 500 mL round bottom flask with soft water (30 mL). The methanol was removed from the round bottom flask with a rotary evaporator, and the solution was then transferred to a 600 mL beaker to which ethyl acetate was added (200 mL). The dispersion was stirred for 30 minutes and transferred to an aluminum-foil wrapped separatory funnel. The liquid phases were phase separated after a couple of hours. The water phase was washed with ethyl acetate (200 mL) and the two decanted ethyl acetate fractions were combined. Soft water (100 mL) was added to the combined ethyl acetate solution and the liquid-liquid dispersion was stirred and neutralized with phosphoric acid. The dispersion was transferred to a separatory funnel and the water layer was decanted and removed. Heptane (100 mL) and soft water (25 mL) was added to the ethyl acetate layer that remained in the separatory funnel and the dispersion was agitated. The water layer was removed and the organic phase was placed on a rotary evaporator at 40-45° C. and 20 inches of pressure until enough ethyl acetate was removed and solids began to form. The slurry was then filtered and this first crop of solids was rinsed with heptane. The yield of the first crop of solids was 0.88 g with a purity of approximately 58% zeaxanthin. The filtrate solution was again placed on the rotary evaporator and the rest of the solvent was removed, producing an oleoresin that contained additional solids. Heptane was added and the solution was filtered to give a second crop of solids. The yield of the second crop of solids was 0.43 g with a purity of about 26% zeaxanthin. Evaporation of the heptane from the second filtrate produced an oleoresin with a color value (American Spice Trade Association Method 20.1) of about 968.

Example 14

A Stabilized Oleoresin

The oleoresin from Example 4 is combined with natural tocopherols, and optionally an edible oil, such that the final concentration of zeaxanthin is 5% and the final concentration of added natural tocopherols is 1%. The resulting fluid is encapsulated into gel capsules suitable for human or animal consumption.

Example 15

A Stabilized Oleoresin

The oleoresin from Example 4 is combined with natural tocopherols, ascorbyl palmitate and optionally an edible oil, such that the final concentration of zeaxanthin is 5% and the final concentration of added natural tocopherols and ascorbyl palmitate is 1%. The resulting fluid is encapsulated into gel capsules suitable for human or animal consumption.

Example 16

A Stabilized Formulation

The zeaxanthin solids from Example 13 are re-esterified with long chain fatty acids. The resulting zeaxanthin esters are formulated with ascorbic acid, natural tocopherols, optionally a vegetable oil and optionally rosemary extract to yield a finished product containing 5% zeaxanthin, 5% ascorbic acid, 5% added natural tocopherols and 0-5% rosemary extract. The resulting fluid is encapsulated into gel capsules suitable for human or animal consumption.

Example 17

A Stabilized Formulation

The zeaxanthin solids from Example 13 are re-esterified with long chain fatty acids. The resulting zeaxanthin esters are formulated with ascorbyl palmitate, natural tocopherols, optionally a vegetable oil and optionally rosemary extract to yield a finished product containing 5% zeaxanthin, 1-5% ascorbyl palmitate, 5% added natural tocopherols and 0-5% rosemary extract. The resulting fluid is encapsulated into gel capsules suitable for human or animal consumption.

Example 18

A Stabilized Formulation

The zeaxanthin solids from Example 13 are dispersed into an edible oil and combined with ascorbic acid, natural tocopherols and optionally rosemary extract to provide a product containing 20% zeaxanthin in free (non-esterified) form, 5% ascorbic acid, 5% tocopherol and 0-5% rosemary extract.

Example 19

A Stabilized Formulation

The zeaxanthin solids from Example 13 are dispersed into an edible oil and combined with ascorbyl palmitate, natural tocopherols and optionally rosemary extract to provide a product containing 20% zeaxanthin in free (non-esterified) form, 5% ascorbyl palmitate, 5% tocopherol and 0-5% rosemary extract.

Example 20

A Stabilized Formulation

The zeaxanthin solids from Example 13 or those solids that have been further purified are dispersed into an edible oil and combined with lutein, ascorbic acid, natural tocopherols and optionally rosemary extract to provide a product containing 0-20% lutein, 1-19% zeaxanthin in free (non-esterified) form, 1-5% ascorbic acid, 5% tocopherol and 0-5% rosemary extract.

Example 21

A Stabilized Formulation

The zeaxanthin solids from Example 13 or those solids that have been further purified are dispersed into an edible oil and combined with lutein, ascorbyl palmitate, natural tocopherols and optionally rosemary extract to provide a product containing 0-20% lutein, 1-19% zeaxanthin in free (non-esterified) form, 1-5% ascorbyl palmitate, 5% tocopherol and 0-5% rosemary extract.

Example 22

A Stabilized Formulation

The oleoresin from Example 4 is combined with natural tocopherols, and olive extractives, such that the final concentration of zeaxanthin is 2% and the final concentration of added natural tocopherols is 1%. The resulting fluid is encapsulated into gel capsules suitable for human or animal consumption.

Example 23

ASTA Procedure (Adapted from ASTA Method 20.1) for Ground Paprika for Samples with and without Seeds Ground, ripe, dried fruit pod flesh with or without seeds of the instant *Capsicum* varieties (1.0 g) was weighed on a top loading balance and was quantitatively transferred to a 125 ml Erlenmeyer flask. 50 ml of acetone was added to the flask. The mixture was homogenized for 1 minute. The solution was vacuum filtered through a Buchner funnel directly into a 100 ml volumetric flask. All the color was rinsed out of the Erlenmeyer flask and the Buchner funnel with acetone, combined and brought to a 100 ml total volume with acetone. A 1 ml sample was pipetted from the 100 ml volumetric into a 25 ml volumetric flask and brought to a total of 25 ml with acetone. The spectrophotometer (Beckman, model: DU650) was set-up for a wavelength scan from 400 nm to 550 nm and was zeroed using an acetone blank. A portion of the solution in the 25 ml volumetric was transferred to the cell and a scan was run from 400 nm to 550 nm. The absorbance at 460 nm was determined. The ASTA was calculated by the following equation:

$$\text{ASTA} = E1\%1CM \times 16.4$$

The calculated percent zeaxanthin based on the ASTA value was calculated using the following formula:

$$\% \text{ Calculated Zeaxanthin} = (E1\%1CM(\text{Sample})/2340^*) \times \% \text{ Zeaxanthin to total Carotenoids}.$$

$$*E1\%1CM \text{ pure zeaxanthin} = 2340$$

Example 24

Concentration of Xanthophyll Pigments by Centrifugation

A quantity of oleoresin containing 6.25% total zeaxanthin, measured as the free zeaxanthin, was processed through a high speed centrifuge. Operating conditions were varied to produce several concentrate fractions, at least one of which contained 12.55% total zeaxanthin, measured as free zeaxanthin. The supernatant from the centrifugation contained an enriched concentration of cryptoxanthin relative to the levels present in the whole extract.

Example 25

Further Random Sampling of Production Fields

Samples of random individual *Capsicum* plants of the present invention were harvested. The pods were dehydrated in a laboratory dehydrator and were subjected to analysis. The concentration of zeaxanthin in the dried fruit flesh was measured by the HPLC method described in Examples 26 and 27. The percentage of zeaxanthin relative to total carotenoids, measured in non-esterified forms, was also measured by the HPLC method described in Example 28, and the analytical result for each sample is shown below. The ASTA value for each sample was also measured by the method described in Example 23, and the corresponding mass percent zeaxanthin was computed from the measured ASTA value. The conversion of the ASTA value into the mass percent zeaxanthin was calculated by the procedure described in Example 23.

| Sample | Total Zeaxanthin in the dried pod with seeds (wt %) | Zeaxanthin/ Carotenoids (area %) | Measured ASTA | Zeaxanthin in the dried pod with seeds Wt % based on ASTA |
|---|---|---|---|---|
| 9300014a | 0.439 | 74 | 246 | 0.474 |
| 9300055a | 0.549 | 66.7 | 329 | 0.572 |
| 9300086a | 0.464 | 64.9 | 299 | 0.506 |
| 9300100a | 0.509 | 56.2 | 359 | 0.526 |
| 9300124a | 0.67 | 61.7 | 450 | 0.723 |
| 9300139a | 0.64 | 61.7 | 408 | 0.656 |
| 9300140a | 0.554 | 65.4 | 351 | 0.598 |
| 9300247a | 0.633 | 64.8 | 405 | 0.648 |
| 9300147a | 0.584 | 79.5 | 256 | 0.53 |
| 9300182a | 0.497 | 65 | 340 | 0.576 |
| 9300254a | 0.437 | 57.9 | 335 | 0.505 |
| 9300277a | 0.484 | 62.6 | 325 | 0.53 |
| 9300305a | 0.401 | 62.2 | 354 | 0.574 |
| 9300326a | 0.457 | 67.2 | 272 | 0.476 |
| 9300345a | 0.507 | 65.1 | 319 | 0.541 |
| 9300360a | 0.462 | 66 | 318 | 0.547 |
| 9300522a | 0.494 | 57.6 | 374 | 0.561 |
| 9300369a | 0.517 | 58.5 | 353 | 0.538 |
| 9300396a | 0.581 | 66.6 | 358 | 0.621 |
| 9300532a | 0.606 | 66.5 | 365 | 0.632 |
| 9300571a | 0.522 | 64.6 | 356 | 0.599 |
| 9300575a | 0.463 | 64.5 | 248 | 0.417 |
| 9300409a | 0.472 | 62.7 | 327 | 0.534 |
| 9300426a | 0.574 | 57 | 366 | 0.544 |
| 9300434a | 0.493 | 62.3 | 320 | 0.519 |
| 9300583a | 0.749 | 69.1 | 395 | 0.711 |
| 9300018a | 0.417 | 60.1 | 304 | 0.476 |
| 9300047a | 0.411 | 66.5 | 244 | 0.423 |
| 9300222a | 0.496 | 78.5 | 201 | 0.411 |
| 9300488a | 0.506 | 63.9 | 255 | 0.425 |
| 9300215a | 0.471 | 63.8 | 295 | 0.490 |

Example 26

Saponification Procedure of Ground *Capsicum* with Seeds for HPLC Analysis

Ground, ripe, dried fruit pod flesh containing seeds of the instant *Capsicum* varieties (0.5 g) was weighed to the nearest tenth of a milligram on an analytical balance and was quantitatively transferred to a 125 ml Erlenmeyer flask. The flask was immediately covered with aluminum foil to reduce exposure to light. Butylated hydroxytoluene (0.2 g, Sigma Chemical Company) and 1.5 g of sodium carbonate powder (Aldrich Chemical—A.C.S. reagent) were weighed and added to the Erlenmeyer flask. 50.0 ml of methanol (Fisher Scientific—HPLC-grade) and 8 pellets (~about 0.8 g) of potassium hydroxide (VWR Intl.) were added to the Erlenmeyer flask. A stir bar was added to the solution and a Vigreux distilling column was attached to the top of the Erlenmeyer flask. The solution was placed on a hot plate and refluxed on low heat (~65° C.) with stirring for 1 hour. Then the solution was taken off the hot plate and allowed to cool. A total of 1.2 ml of phosphoric acid (JT Baker—A.C.S. Reagent) was added to neutralize the solution. The solution was vacuum filtered through a Buchner funnel containing Celite® (Eagle Picher Filtration and Minerals, Reno, Nev.) directly into a 200 ml volumetric flask. All the color was rinsed out of the Erlenmeyer flask and the Buchner funnel with methanol, combined and brought to a 200 ml total volume with methanol. After inverting the flask several times, the solution was poured into a 3 cc syringe with a 0.45 micron PTFE Acrodisc® (Gelman) filter and injected into an amber vial for HPLC analysis.

Example 27

Determination of Zeaxanthin Content (Wt %) by HPLC in *Capsicum* Pods with and without Seeds The analyses were performed on a Waters 2695 (Milford, Mass. USA) separation system using Empower (Build 1154, Database version 5.00.00.00) software installed on the data station. The chromatographic separation was performed on a reverse-phase column (Waters Symmetry® C18, particle size 5 μm, 250 mm×4.6 mm). The eluent was a ternary gradient of methanol/water/acetone at 1.0 ml/min. The initial composition of the eluent was methanol-water-acetone (0:25:75, v/v/v). An initial linear gradient was applied for 15 minutes and yielded a composition of methanol-water-acetone (20:5:75, v/v/v). This composition was held for 15 minutes, followed by another linear gradient for 5 minutes to yield a composition of methanol-water-acetone (0:0:100, v/v/v) and held for 5 minutes. Another linear gradient was applied for 5 minutes to initial conditions and held for 15 minutes before next injection. Compounds were detected photometrically (max-plot between 400 nm-600 nm) on a Waters 2996 photodiode array detector using an injection volume of 20.0 μl. Zeaxanthin content was measured in reference to a calibration curve generated from a purchased authentic sample. Trans-zeaxanthin obtained from Indofine Chemical Company, Inc. and was dissolved in 90% acetone/10% acetone containing 6% glacial acetic acid. This stock solution was diluted in acetone and run on a Beckman Coulter DU640 spectrophotometer at 452 nm. This absorbance was used with an E1% of 2340 to calculate the concentration of stock solution. The stock solution was then diluted down with acetone to generate a 5-point external calibration curve covering concentrations ranging from 4.0 μg/ml-75.0 μg/ml with a linear fit. 9-cis-zeaxanthin was quantified using the trans-zeaxanthin calibration curve, assuming a response factor of 1:1. Zeaxanthin contents are reported as a sum of all zeaxanthin isomers. A system check sample (DSM Zeaxanthin 20% FS; Product Code: 5002001; Lot: UE00303001) was run on the day of analysis at a level between 25.0 μg/ml-45.0 μg/ml. Results were corrected only if check sample was not within 5% of the expected value.

Example 28

Determination of the Percentage of Zeaxanthin Relative to Total Carotenoids (Area %) by HPLC for *Capsicum* Pods with and without Seeds Analyses were performed on a Waters 2695 (Milford, Mass. USA) separation system using Empower (Build 1154, Database version 5.00.00.00) software installed on the data station. The chromatographic separation was performed on a reverse-phase column (Waters Symmetry® C18, particle size 5 μm, 250 mm×4.6 mm). The eluent was a ternary gradient of methanol/water/acetone at 1.0 ml/min. The initial composition of the eluent was methanol-water-acetone (0:25:75, v/v/v). An initial linear gradient was applied for 15 minutes and yielded a composition of methanol-water-acetone (20:5:75, v/v/v). This composition was held for, 15 minutes, followed by another linear gradient for 5 minutes to yield a composition of methanol-water-acetone (0:0:100, v/v/v) and held for 5 minutes. Another linear gradient was applied for 5 minutes to initial conditions and held for 15 minutes before next injection. Compounds were detected photometrically (max-plot between 400 nm-600 nm) on a Waters 2996 photodiode array detector using an injection volume of 20.0 μl. Literature retention times and PDA spectra were used to identify some of the peaks (violoxanthin, antheraxanthin, 9-cis-zeaxanthin, cryptocapsin, α-cryptoxanthin, ζ-carotene). Other compounds were identified and compared with standards from Carotenature (Lupsingen, Switzerland) and are listed as follows: capsorubin, capsanthin, trans-zeaxanthin, lutein, β-cryptoxanthin, α-carotene, trans-β-carotene and cis-β-carotene.

Example 29

Saponification Procedure of Ground *Capsicum* without Seeds for HPLC Analysis

Ripe, dried fruit pod flesh of the instant *Capsicum* varieties (0.5 g), without seeds, was ground and weighed to the nearest tenth of a milligram on an analytical balance and was quantitatively transferred to a 125 ml Erlenmeyer flask. The flask was immediately covered with aluminum foil to reduce exposure to light. Butylated hydroxytoluene (0.2 g, Sigma Chemical Company) and 1.5 g of sodium carbonate powder (Aldrich Chemical—A.C.S. reagent) were weighed and added to the Erlenmeyer flask. 50 milliliters of methanol (Fisher Scientific—HPLC-grade) and 8 pellets (~about 0.8 g) of potassium hydroxide (VWR Intl.) were added to the Erlenmeyer flask. A stir bar was added to the solution and a Vigreux distilling column was attached to the top of the Erlenmeyer flask. The solution was placed on a hot plate and refluxed on low heat (~65° C.) with stirring for 1 hr. Then the solution was taken off the hot plate and allowed to cool. A total of 1.2 ml of phosphoric acid (JT Baker—A.C.S. Reagent) was added to neutralize the solution. The solution was vacuum filtered through a Buchner funnel containing Celite® (Eagle Picher Filtration and Minerals, Reno, Nev.) directly into a 200 ml volumetric flask. All the color was rinsed out of the Erlenmeyer flask and the Buchner funnel with methanol, combined and brought to a 200 ml total volume with methanol. After inverting the flask several times, the solution was poured into a 3 cc syringe with a 0.45 micron PTFE Acrodisc® (Gelman) filter and injected into an amber vial for HPLC analysis.

Example 30

Analysis of *Capsicum* without Seeds

Samples of random individual *Capsicum* plants of the instant invention were harvested. The pods were deseeded and dehydrated in a laboratory dehydrator and were treated along the lines of Example 29 for analysis. The concentration of zeaxanthin in the dried fruit flesh was measured by the HPLC method described in Example 27. The percentage of zeaxanthin relative to total carotenoids, measured in nonesterified forms, was also measured by the HPLC method described in Example 28, and the analytical result for each sample is shown below.

| Sample | Total Zeaxanthin in the dried pod without seeds (wt %) | Zeaxanthin/ Carotenoids (area %) |
|---|---|---|
| 9300014b | 0.55 | 65.9 |
| 9300055b | 0.424 | 63.5 |
| 9300098b | 0.783 | 61.8 |
| 9300124b | 0.849 | 59.6 |
| 9300043b | 0.624 | 64.4 |
| 9300050b | 0.783 | 59.2 |
| 9300080b | 0.634 | 62.2 |
| 9300086b | 0.517 | 57.5 |
| 9300289b | 0.582 | 63.7 |
| 9300158b | 0.748 | 63.3 |
| 9300336b | 0.844 | 64 |
| 9300358b | 0.678 | 65.2 |
| 9300450b | 0.742 | 64.8 |
| 9300473b | 0.693 | 69.7 |
| 9300486b | 0.711 | 64.8 |

Example 31

HPLC Separation of the Pigments

Both the red paprika and the instant orange paprika contain some unidentified pigments and their spectra indicate that there are alternate biosynthetic pathways operating in the red paprikas compared to orange paprikas. Up to about 40% or more of the pigments in the yellows are currently not identified by HPLC. Because of these significant differences, the yellow types are not further considered.

Many of the lesser pigments in the reds and oranges are intermediates in the conversion of α- and β-carotene to their diol derivatives. For example, the cryptoxanthins are present in very different concentrations, as is violaxanthin, a precursor of capsorubin. Because these intermediates are present in relatively low amounts, they are not included in Table 3. below. Their relative amounts to total pigment contents may represent some variation in the actual maturity of the pods. The amounts are insufficient to affect the distinction between the classes, and may portray biochemical differences between the red-fruited and orange-fruited strains.

TABLE 3

Key pigment ratios distinguishing orange-colored from red-colored paprikas.

| | | ASTA | Zeaxanthin (Trans + Cis) % | Lutein % | Capsanthin + Capsorubin % | Lutein/ Zeaxanthin Ratio | α-Carotene/ β-Carotene Ratio | Capsanthin/ Zeaxanthin Ratio |
|---|---|---|---|---|---|---|---|---|
| Reds | Mean = | 464.64 | 13.04 | 5.83 | 33.17 | 0.50 | 0.02 | 2.52 |
| | STD = | | 4.69 | 0.71 | 3.13 | 0.17 | 0.01 | 0.79 |
| Oranges | Mean = | 360.70 | 68.48 | 0.92 | 4.36 | 0.02 | 0.05 | 0.06 |
| | STD = | | 5.12 | 0.65 | 2.04 | 0.01 | 0.10 | 0.03 |

Table 3. shows the key differences between the level of pigments in representative types of red and orange paprikas. It will be noted that capsorubin and capsanthin predominate in the red-fruited strains, whereas zeaxanthin predominates in the orange-fruited strains and the level of the red pigments is about half or less of that in the red strains. The zeaxanthin level observed in the orange-fruited strains is ~4-5 times higher than that observed in the red-fruited strains on a relative basis. The lutein level observed in the orange-fruited strains is ~5-6 times less than in the red strains on a relative basis. The sum of capsanthin plus capsorubin observed in the orange-fruited strains is ~7-8 times less than in reds on a relative basis. The ratio of lutein to zeaxanthin observed in the orange-fruited strains is ~25 times less than in reds on a relative basis. The ratio of α-carotene to β-carotene observed in the orange-fruited strains is ~2 times more than in red-fruited strains on a relative basis. The ratio of capsanthin to zeaxanthin in the orange-fruited strains is ~42 times less than in the red strains on a relative basis. The analysis affirms that there are differences in the carotenoid biosynthetic pathways between the instant orange paprika and red paprika strains described herein.

It should be noted that ASTA is used as a proxy for molar or weight ratios of pigments. ASTA utilizes the absorbance of a solution of the extract at a wavelength of 460 nm. The orange paprikas have a lambda maximum at 454-455 nm, whereas the red paprikas have a lambda max close to 460 nm. Therefore, the ASTA of equal pigment content is somewhat lower for an orange paprika than a red paprika. From the standpoint of separating the genotypes, this does not make a difference. It should also be noted that in field sampling, there is always a variation in ASTA observed on a single plant and between different plants of the same strain. This is due to variations in maturity, disease and other stresses, as well as field soil differences.

Table 3. presents reasonable average values for ASTAs and HPLC ratios for the purpose of demonstrating the distinct biochemical differences between the red-fruited strains and the instant orange-fruited strains. Individual pods from the same or different plants may have different pigment ratios and ASTAs. The averages show what may be reasonably expected from a normal crop derived from these paprikas.

The instant orange paprikas were developed by careful hybridization, selection of superior plants which, through recombination of genes or promoters, modified the carotenoid pathway without reducing the pigment content. The orange strains are comparable to commercial red paprikas in ASTA, but with a novel pigment profile, high in zeaxanthin, which has a distinctly different absorption spectrum than the reds. Therefore a strain or strains of a *Capsicum annuum* paprika type cultivar is the preferred type of *Capsicum* as the source of zeaxanthin. It is commercially attractive if zeaxanthin is present at more than about 50% of the area count of the total pigments. As the area count % increases to 65%, further to 75%, and even further to 80%, the cost of the zeaxanthin is reduced. It is also the preferred source of an oleoresin rich in zeaxanthin.

Deposit Information:

Applicant has deposited at least 2500 seeds of *Capsicum annuum* NM 1441 disclosed herein with the American Type Culture Collection (ATCC), 10801 University Boulevard, Manassas, Va. 20110-2209 USA under the terms of the Budapest Treaty. The accession number for the deposit is ATCC Accession No. PTA-10729 and the date of deposit is Mar. 25, 2010. Access to this deposit will be available during the pendency of the application to the Commissioner of Patents and Trademarks and persons determined by the Commissioner to be entitled thereto upon request.

In accord with 37 CFR §1.808, the Applicant declares that all restrictions imposed by the depositor on the availability to the public of the deposited material will be irrevocably removed upon the granting of the patent. Moreover, Applicant reserves the right to contract with the depository to require that samples of a deposited biological material shall be furnished only if a request for a sample, made during the term of the patent:

(1) Is in writing or other tangible form and dated;
(2) Contains the name and address of the requesting party and the accession number of the deposit; and
(3) Is communicated in writing by the depository to the depositor along with the date on which the sample was furnished and the name and address of the party to whom the sample was furnished.

REFERENCES

Abel, R. Jr., 2004, The Eye Care Revolution: Prevent and Reverse Common Vision Problems, Kensington Publishing Corp., NY, N.Y. ISBN 0-7582-0622-4, p. 159.

Abellan-Palazon, M., 2001, Effect of Titanium Ascorbate Treatment on Red and Yellow Pigment Composition of Paprika Cultivars, Acta Alimentaria, Vol. 30 (2), pp. 159-171.

Ahmed S. et al., 2005, The Macular Xanthophylls. Surv Ophthalmol., 50(2), pp 183-93.

Almela, L. et al., 1991, Carotenoid Composition of New Cultivar of Red Pepper for Paprika, J. Agric. Food Chem., 39, pp. 1606-1609.

Almela, L. et al., 1996, Changes in Pigments, Chlorophyllase Activity and Chloroplast Ultrastructure in Ripening Pepper for Paprika, J. Agric. Food Chem. 44, pp. 1704-1711.

Alves-Rodrigues A, and Shao A., 2004, The Science Behind Lutein. Toxicol Lett. April 15, 150(1), pp. 57-83.

Antony, J. I. X and Shankaranarayana, M. L., 2001, Lutein—A Natural Colorant and a Phytonutrient For Eye Health Protection, The World of Food Ingredients, April/May, pp. 64-67.

Aranson, J. T. et al., 1995, Fate of Phototoxic Terthiophene Insecticides in Organisms and the Environment in Light-Activated Pest Control, ACS Symposium Series 616, J. R. Heitz and K. R. Downum, eds., American Chemical Society, Washington D.C., pp. 143-151.

Banaras, M. et al., 1994, Relationship of Physical Properties to Postharvest Water Loss on Pepper Fruits (*Capsicum annuum* L.), Pak. J. Bot., 26(2), pp. 321-326.

Beatty S. et al., 2004, Macular Pigment Optical Density and Its Relationship With Serum and Dietary Levels of Lutein and Zeaxanthin. Arch Biochem Biophys., 430(1), pp. 70-6.

Biacs, P. et al., 1993, Carotenoids and Carotenoid Esters from New Cross-Cultivars of Paprika, J. Agric. Food Chem., 41, pp. 1864-1867.

Biacs, P. and Daood, H., 1994, High Performance Liquid Chromatography with Photodiode-array Detection of Carotenoids and Carotenoid Esters in Fruits and Vegetables, J. Plant Physiol. Vol. 143, pp. 520-525

Bouvier F, et al., 1994, "Xanthophyll Biosynthesis in Chromoplasts: Isolation and Molecular Cloning of An Enzyme Catalyzing The Conversion of 5,6-Epoxycarotenoid Into Ketocarotenoid," Plant Journal 6, pp. 45-54.

Bowen, P. E., et al., 2002, Esterification Does Not Impair Lutein Bioavailability in Humans, J. Nutr. 132, pp. 3668-3673.

Breithaupt, Dietmar E., et al.; British Journal of Nutrition, (2004), 91, pp. 707-713.

Breithaupt, Dietmar E. & Schlatterer, Jorg; Eur Food Res Technol, (2005) 220, pp. 648-652.

Breithaupt, D. E., and Bamedi, A., 2001, Carotenoid Esters in Vegetables and Fruits: A Screening with Emphasis on β-Cryptoxanthin Esters, J. Agric. Food Chem., 49, pp. 2064-2070.

Brown L. et al., 1999, A Prospective Study of Carotenoid Intake and Risk of Cataract Extraction in US Men. Am J Clin Nutr., 70(4), pp. 517-24.

Camara, Bilal & Moneger, Rene; Phytochemistry, 1978, Vol. 17, pp. 91-93

Connor S. et al., 2004, Diets Lower in Folic Acid and Carotenoids Are Associated with The Coronary Disease Epidemic in Central and Eastern Europe. J Am Diet Assoc. 104(12): pp. 1793-9.

Davies, N. P. et al., 2004, Macular Pigments: Their Characterization and Putative Role, Prog. Ret. Eye Res. 23, pp. 533-559.

Deli, J. et al., 1992, Carotenoid Composition in the Fruits of Black Paprika (*Capsicum annuum* Variety *longum nigrum*) during Ripening, J. Agric. Food Chem., 40, pp. 2076.

Deli, J. et al., 1996, Carotenoid Composition in the Fruits of *Capsicum annuum* Cv. Szentesi Kosszarvu during Ripening, J. Agric. Food Chem., 44, pp. 711-716.

Deli, J., and G. Toth, 1997, Carotenoid Composition of The Fruits of *Capsicum annuum* Cv. Bovet 4 During Ripening," Z Lebensm Unters Forsch A, 205, pp. 388-391.

Deli, J. et al., 2001, Carotenoid Composition in the Fruits of Red Paprika (*Capsicum annuum* var. *lycospersiciforme rubrum*) During Ripening: Biosynthesis of Carotenoids in Red Paprika," J. Agric. Food Chem., 49, pp. 1517-1523.

Deruere, J., et al., 1994, The Plant Cell, Vol. 6, pp. 119-133

Downum, K. R. and J. Wen, 1995, "The Occurrence of Photosensitizers Among Higher Plants", in *Light-Activated Pest Control*, ACS Symposium Series 616, J. R. Heitz and K. R. Downum, eds., American Chemical Society, Washington D.C., pp. 135-143.

Englert, G. et al, 1991, Helv. Chim. Acta., 74, pp. 969-982.

Evans et al., 1993, Handbook of Plant Cell Culture, MacMillian Publishing Co., NY Fisher, C. and Kocis, J. A., 1987, *J. Agric. Food Chem.* 35, pp. 55-57.

Gelvin et al., 1990, Plant Molecular Biology Manual, Kluwer Academic Publishers

Green et al., 1987. Plant Tissue & Cell Culture, Academic Press, NY

Hausen, B. M., and B. Helmke, 1995, "Butenylbithiophene, α-terthienyl and Hydroxytremetone As Contact Allergens in Cultivars of Marigold (*Tagetes* sp.)," Cont. Derm. 33, pp. 33-37.

Hirschberg, J., 2001, "Carotenoid Biosynthesis in Flowering Plants," Current Opinions in Plant Biology 4(3), pp. 210-218.

Hornero-Mendez, D. et al., 2002, "Characterization of Carotenoid High-Producing *Capsicum annuum* Cultivars Selected for Paprika Production," J. Agric. Food Chem., 50, pp. 5711-5716.

Ishida, B. K., et al, 2005, Assessing Bioavailability of cis-vs trans-lycopene isomers in Tangerine and Red Tomatoes, Carotenoid Science, Vol. 9, pp. 92.

Isler, O. et al, 1956, Helv. Cim. Acta., 39, p. 249

Ito Y, et al, 2005, JACC Study Group. Lung Cancer Mortality and Serum Levels of Carotenoids, Retinol, Tocopherols, and Folic Acid in Men and Women: A Case-Control Study Nested in The JACC Study. J. Epidemiol. Suppl 2:S140-9. PMID: 16127226

Kahl et al., (1995) World Journal of Microbiology and Biotechnology 11, pp. 449-460

Karrer, P. and Jucker, E., 1950, Carotenoids, Elsevier Publ. Co., Inc., Amsterdam, pp. 38-42, 180 ff Khachik, F. et al., 1992, Isolation and Structural Elucidation of the Geometrical Isomers of Lutein and Zeaxanthin in Extract from Human Plasma, J. Chromatogr. Biomed. Appl. 582, pp. 153-166.

Khachik, F., et al., 1995, Lutein, Lycopene, and Their Oxidative Metabolites in Chemo-prevention of Cancer, J. Cell. Biochem., Suppl. 22, pp. 236-246.

Khachik F, et al., 1997, Identification of Lutein and Zeaxanthin Oxidation Products in Human and Monkey Retinas. Invest Ophthalmol Vis Sci., pp. 1802-11.

Khachik, F. et al., 1999, Dietary Carotenoids and their Metabolites as Potentially Useful Chemoprotective Agents against Cancer, in Antioxidant Food Supplements in Human Health, L. Packer, M. Hiramatsu and T. Yoshikawa, eds., Academic Press, NY, pp. 203-229.

Klee et al., 1987, Ann. Rev. of Plant Phys. 38, pp. 467-486

Kohlmeier, L. et al., 1995, Am. J. Clin. Nutr. 62, pp. 137-146

Levy, Joseph, et al., 1995, Lycopene Is a More Potent Inhibitor Of Human Cancer Cell Proliferation Than Either α-Carotene or β-Carotene," Nutrition & Cancer, pp 257-266.

Lutein and Zeaxanthin Scientific Review, Roche Vitamins Technical Publication HHN-1382/0800

Lyle B J, et al., 1999, Antioxidant Intake and Risk of Incident Age-Related Nuclear Cataracts in The Beaver Dam Eye Study., Am J. Epidemiol., pp. 801-9.

Matus et al., 1991, Carotenoid Composition of Yellow Pepper during Ripening: Isolation of β-Cryptoxanthin 5,6-Epoxide, J. Agric. Food Chem., 39, pp. 1907-1914.

Minguez-Mosquera, M. I. et al., 1993, Effect of Processing of Paprika on the Main Carotenes and Esterified Xanthophylls Present in the Fresh Fruit, J. Agric. Food Chem., 41, pp. 2120-2124.

Minguez-Mosquera, M. I. et al., 1994, Comparative Study of the Effect of Paprika Processing on the Carotenoids in Peppers (*Capsicum annuum*) of the Bola and Agridulce Varieties, J. Agric. Food Chem., 42, 1555-1560.

Minguez-Mosquera, M. and Hornero-Mendez, D., 1994, Changes in Carotenoid Esterification during the Fruit Ripening of *Capsicum annuum* Cv. Bola, J. Agric. Food Chem., 42, pp. 640-644.

Minguez-Mosquera, M. and Hornero-Mendez, D., 1993 Separation and Quantification of the Carotenoid Pigments in Red Peppers (*Capsicum annuum* L.), Paprika, and Oleoresin by Reversed-Phase HPLC, J. Agric. Food Chem., 41, pp. 1616-1620.

Muller, H., 1997, Determination of the carotenoid content in selected vegetables and fruit by HPLC and Photodiode array detection, Z. Lebensm Unters Forsch A., 204, pp. 88-94

Murakoshi et al., 1992, Cancer Res., 52, pp. 6583-6587

Nys, Y. Arch. Geflugelk, 2000, 64 (2), pp. 45-54

Osganina S., et al., 2003, Dietary Carotenoids and Risk of Coronary Artery Disease in Women, Am. J. Clin. Nutr. 2003 June; 77(6), pp. 1390-1393.

Packer. L. et al., (Editors), 1999, Antioxident Food Supplements in Human Health, Academic Press, NY, pp 223-226.

Pattison, D., 2005, American Journal of Clinical Nutrition, Pub. by American Society for Clinical Nutrition, Vol. 82, No. 2, pp. 451-455

Rahman, R. M. M., and K. A. Buckle, 1980, "Pigment Changes in *Capsicum* Cultivars During Maturation and Ripening", J. Fd. Technol., 15, pp. 241-249.

Ribaya-Mercado J. et al., 2004, Lutein and Zeaxanthin and Their Potential Roles in Disease Prevention. J. Am. Coll. Nutr., 23(6 Suppl), pp. 567S-587S.

Rock C. et al., 2005, Plasma Carotenoids and Recurrence-free Survival in Women with a History of Breast Cancer. J. Clin. Oncol., pp. 6631-8.

Russo, V. M. and Howard, L. R. *J. Sci. Food Agric.* 82: 615-624.

Seddon, J. M. et al., 1994, Dietary Carotenoids, Vitamins A, C, and E, and Advanced Age-Related Macular Degeneration," J. Am. Med. Assoc. 272(9), pp. 1413-1420.

Sommerburg, Olaf, et al.; Br F Ophthalmol. 1999, 82, pp. 907-910.

Stahl W., 2005, Macular Carotenoids: Lutein and Zeaxanthin. Dev Ophthalmol. 38, pp. 70-88.

Stahl W. and Sies H., 2005, Bioactivity and Protective effects of Natural Carotenoids. Biochim Biophys Acta., 1740(2), pp. 101-7. Epub 2004 Dec. 28.

Stringham J. and Hammond B. Jr., 2005, Dietary Lutein and Zeaxanthin: Possible Effects on Visual Function, Nutr. Rev. 63(2), pp. 59-64.

Tanaka et al., 1994, Carcinogenesis 15, pp. 15-19

Topuz, A. and Ozdemir, F., 2003, Influences of γ-Irradiation and Storage on the Carotenoids of Sun-Dried and Dehydrated Paprika, J. Agric. Food Chem., 51, pp. 4972-4977.

Updike, A. A., and Schwartz, S. J., 2003, Thermal Processing of Vegetables Increases the Cis Isomers of Lutein and Zeaxanthin, J. Agric. Food Chem. 51, pp. 6184-6190.

Vasil., 1984, Cell Culture and Somatic Cell Genetics of Plants, Vol I, II, III, Laboratory Procedures and Their Applications, Academic Press, NY Weissbach and Weissbach, 1989, Methods for Plant Molecular Biology, Academic Press Weller, P. and Breithaupt, D., 2003, Identification and Quantification of Zeaxanthin Esters in Plants Using Liquid Chromatography-Mass Spectrometry, J. Agric. Food Chem., 51, pp. 7044-7049.

Yin et al., 2004, Transgene Inheritance In Plants. J. Appl. Genet. 45(2), pp. 127-144 and references therein.

Zechmeister, L., 1962, *Cis-Trans Isomeric Carotenoids Vitamins A and Arylpolyenes*, Academic Press, pp. 46-57.

Zhou, L. et al., 1999, The Identification of Dipalmityl Zeaxanthin as the Major Carotenoid in Gou Qi Zi by High Pressure Liquid Chromatography and Mass Spectrometry, J. Ocular Pharm. and Therap., 15(6), pp. 557-565.

The invention claimed is:

1. An isolated *Capsicum annuum* paprika plant, or regenerable portion thereof, which plant is obtained by inbreeding *Capsicum annuum* NM 1441, deposited at the American Type Culture Collection (ATCC) under accession number PTA-10729, and selecting for a plant which produces orange ripe fruit pods, and which plant exhibits zeaxanthin in the dried ripe fruit pod flesh, wherein the mass of zeaxanthin, when measured in non-esterified form, is greater than 0.4% of the mass of total dried ripe fruit pod flesh and wherein zeaxanthin is the dominant carotenoid, when measured in non-esterified forms.

2. The isolated *Capsicum annuum* paprika plant, or regenerable portion thereof, of claim 1, wherein the percentage of zeaxanthin relative to the percentage of total carotenoids in the dried, ripe fruit pod flesh is greater than 50% as determined by HPLC area count.

3. The isolated *Capsicum annuum* paprika plant, or regenerable portion thereof, of of claim 1, characterized by a zeaxanthin content of greater than 60% of the percentage of total pigments as determined by HPLC area count.

4. The isolated *Capsicum annuum* paprika plant, or regenerable portion thereof, of of claim 1, characterized by a zeaxanthin content of greater than 70% of the percentage of total pigments as determined by HPLC area count.

5. The isolated *Capsicum annuum* paprika plant, or regenerable portion thereof, of claim 1, wherein the mass of zeaxanthin is greater than 0.7% of the total dried ripe fruit pod flesh.

6. The isolated *Capsicum annuum* paprika plant, or regenerable portion thereof, of claim 1, wherein the mass of zeaxanthin is greater than 0.8% of the total dried ripe fruit pod flesh.

7. The isolated *Capsicum annuum* paprika plant, or regenerable portion thereof, of claim 1, wherein the mass of zeaxanthin is greater than 0.9% of the total dried ripe fruit pod flesh.

8. The isolated *Capsicum annuum* paprika plant, or regenerable portion thereof, of claim 1, characterized by a capsanthin plus capsorubin content of less than 10% of the percentage of total pigments as determined by HPLC area count.

9. The isolated *Capsicum annuum* paprika plant, or regenerable portion thereof, of claim 1, characterized by a capsanthin plus capsorubin content of less than 7% of the percentage of total pigments as determined by HPLC area count.

10. The isolated *Capsicum annuum* paprika plant, or regenerable portion thereof, of claim 1, wherein the regenerable portion is selected from embryos, meristems, pollen, leaves, anthers, ovules, roots, root tips, fruit pods, seeds, petals, flowers, protoplasts and callus obtained therefrom.

11. A cell culture or tissue culture of the *Capsicum annuum* paprika plant, or regenerable portion thereof, of claim 1.

12. A grafted plant or progeny of the regenerable portion of the isolated *Capsicum annuum* paprika plant of claim 1, wherein said grafted plant or progeny produces orange ripe fruit pods and which plant exhibits zeaxanthin in the dried ripe fruit pod flesh, wherein the mass of zeaxanthin, when measured in non-esterified form, is greater than 0.4% of the mass of total dried ripe fruit pod flesh and wherein zeaxanthin is the dominant carotenoid, when measured in non-esterified forms.

13. A seed, which yields the *Capsicum annuum* paprika plant of claim 1.

14. A fresh or dried fruit of the plant of the *Capsicum annuum* paprika plant of claim 1, in either whole or comminuted form.

* * * * *

UNITED STATES PATENT AND TRADEMARK OFFICE
CERTIFICATE OF CORRECTION

PATENT NO. : 8,592,662 B2  
APPLICATION NO. : 13/134185  
DATED : November 26, 2013  
INVENTOR(S) : Paul H. Todd, Jr. et al.

Page 1 of 1

It is certified that error appears in the above-identified patent and that said Letters Patent is hereby corrected as shown below:

Title Page, Item (56)  
References Cited Page 2 column 1:  
"Czinkotai, B., et al.; Hournal of Liquid Chromatography"  
should be  
--Czinkotai, B., et al.; Journal of Liquid Chromatography--.

References Cited Page 3 column 2:  
"Downum, K.R. and J. Wen,"  
should be  
--Downum, K.R. and J. Wen, 1995--.

In the Claims

Column 44, Line 10: "of of Claim 1" should be --of claim 1--.

Column 44, Line 14: "of of Claim 1" should be --of claim 1--.

Signed and Sealed this  
Fifteenth Day of April, 2014

Michelle K. Lee  
*Deputy Director of the United States Patent and Trademark Office*